(12) United States Patent
Broyer et al.

(10) Patent No.: US 9,957,473 B2
(45) Date of Patent: May 1, 2018

(54) DEVICE FOR PREPARING BIOLOGICAL SAMPLES

(71) Applicant: BIOMÉRIEUX, Marcy l'Etoile (FR)

(72) Inventors: Patrick Broyer, Saint Cassien (FR); Laurent Veron, Villeurbanne (FR); Hervé Rostaing, Le Versoud (FR)

(73) Assignee: BIOMERIEUX, Marcy l'etoile (FR)

( * ) Notice: Subject to any disclaimer, the term of this patent is extended or adjusted under 35 U.S.C. 154(b) by 0 days. days.

(21) Appl. No.: 14/782,757

(22) PCT Filed: Apr. 22, 2014

(86) PCT No.: PCT/FR2014/050973
§ 371 (c)(1),
(2) Date: Oct. 6, 2015

(87) PCT Pub. No.: WO2014/174203
PCT Pub. Date: Oct. 30, 2014

(65) Prior Publication Data
US 2016/0040115 A1 Feb. 11, 2016

(30) Foreign Application Priority Data

Apr. 24, 2013 (FR) .................................... 13 53755
Oct. 14, 2013 (FR) .................................... 13 59952

(51) Int. Cl.
*C12M 1/26* (2006.01)
*G01N 1/40* (2006.01)

(52) U.S. Cl.
CPC ............ *C12M 33/04* (2013.01); *C12M 33/14* (2013.01); *G01N 1/40* (2013.01)

(58) Field of Classification Search
CPC ...... B01L 3/50255; B01L 3/5635; B01L 9/50; B01L 9/52; B01L 2300/0681; B01L 2300/0877; G01N 1/4005
See application file for complete search history.

(56) References Cited

U.S. PATENT DOCUMENTS

| 4,052,163 | A | * | 10/1977 | Patzner | ................ | B01D 29/012 |
| | | | | | | 210/406 |
| 4,722,792 | A | * | 2/1988 | Miyagi | .................. | B01D 33/11 |
| | | | | | | 210/360.1 |
| 6,280,621 | B1 | * | 8/2001 | Yazawa | .................. | B01D 61/18 |
| | | | | | | 210/248 |

(Continued)

OTHER PUBLICATIONS

Oct. 27, 2015 International Preliminary Report on Patentability issued in International Patent Application No. PCT/FR2014/050973.

(Continued)

*Primary Examiner* — Brian R Gordon
(74) *Attorney, Agent, or Firm* — Oliff PLC

(57) ABSTRACT

A device for preparing biological samples including a fixed support of which the base extends in a first plane, a filtration block that can be removable, the filtration block including a collecting tank that itself includes a filtering device extending in a second plane and dividing the collecting tank into a collection area and a suction area, the suction area being designed to be connected to a suction device, the second plane of the filtering device being inclined relative to the plane of the base of the fixed support.

17 Claims, 12 Drawing Sheets

(56) References Cited

U.S. PATENT DOCUMENTS

| | | | | |
|---|---|---|---|---|
| 6,458,278 | B1 * | 10/2002 | Leoncavallo | B01D 29/05 210/321.75 |
| 7,470,535 | B2 * | 12/2008 | Yang | G01N 13/00 210/321.75 |
| 8,518,246 | B2 * | 8/2013 | Lendenfeld | C12M 33/14 210/120 |
| 2004/0038425 | A1 | 2/2004 | Ferguson et al. | |
| 2007/0298451 | A1 | 12/2007 | Ribault et al. | |
| 2008/0290040 | A1 | 11/2008 | Kane et al. | |
| 2011/0315641 | A1 | 12/2011 | Curran et al. | |

OTHER PUBLICATIONS

Aug. 20, 2014 International Search Report issued in International Patent Application No. PCT/FR2014/050973.

* cited by examiner

Lysis-filtration using the device according to the invention on inoculated blood cultures ($D_0$)

DEVICE FOR PREPARING BIOLOGICAL SAMPLES

BACKGROUND

The field of the present invention is that of microbiological analysis. More particularly, the present invention relates to a device for preparing a biological sample with a view to a microbiological diagnosis.

Vacuum filtration is conventionally used in laboratories. It is used in two ways:
  either to clarify a sample. The filtrate is then kept and the filter discarded,
  or to collect and concentrate particles or microorganisms of interest present in a liquid sample. In this second case, the filtrate is discarded, and the concentrate (also called retentate) and/or the filter are kept.

A known device from the prior art is the Büchner funnel. Such a device is represented in FIG. 1. It comprises a funnel in which a perforated plate is transversely positioned. The funnel is fitted in a leaktight manner into the neck of a vacuum flask by means of a bung. The vacuum flask is connected to a suction source. A filter paper is placed on the perforated plate, said filter paper having been moistened so that particles present in a liquid poured onto the upper part of the paper can be retained during the suction. The liquid filtered, or filtrate, is collected in the flask.

Such a device has several drawbacks. Indeed, the filter can become rapidly blocked if the liquid contains too many particles or microorganisms, which can prevent filtration of the entire volume. Furthermore, the large filtration surface area, required in order to be able to filter a sufficient amount of sample, can require the use of a large volume of liquid for completely resuspending the microorganisms retained on the filter, which does not make it possible to have an optimal concentration ratio.

After having filtered the sample by means of this device, the collection of particles of interest or microorganisms retained on the filter paper is difficult and requires the manual use of a swab. It is not easy to reproducibly perform the recovery by swab automatically. Furthermore, this type of device has an unfavorable second release yield if the concentrate, in particular bacterial concentrate, must be provided in liquid form for the needs of the analysis protocol. Finally, during the steps of washing the filter or of taking up the microorganisms with a pipette, the liquid dispensed spreads over the entire surface of the filter, and it is therefore difficult to again suction it. As a result, the sequence of a filtration protocol using this device cannot be easily automated.

Another device of the prior art, described in patent application US 2007/0298451 A1, comprises a lower filtration block and an upper filtration block. The upper filtration block comprises a cylindrical wall having a first diameter and a cylindrical wall having a smaller diameter, connected by a transverse part. A perforated plate and also a filtration membrane are placed on the transverse part. The lower filtration block comprises a cylindrical wall having a first diameter and a cylindrical wall having a smaller diameter connected by a transverse part. A perforated plate and also a filtration membrane are placed on the transverse part. A cylindrical wall having an even smaller diameter is placed downstream of the perforated plate and connected to the lower filtration block by a transverse part, so as to connect a suction source to the device.

The upper filtration block is fitted onto the lower filtration block. The membrane of the upper filtration block has a porosity greater than the membrane of the lower filtration block. As a result, when a liquid sample is poured onto the membrane of the upper filtration block and the suction source is activated, said sample is filtered a first and then a second time.

Although this device can have a better filtration yield, in particular if progressive filtrations are carried out, the liquid dispensed also spreads over the entire surface of the two membranes, making collection difficult. Furthermore, blocking, even partial, of one or more membrane(s) can lead to a pressure drop during suctioning and slow down or even prevent filtration.

BRIEF SUMMARY

The aim of the invention is therefore to remedy the abovementioned prior art drawbacks.

A first objective of the present invention is thus to provide a device for treating a biological sample which makes it possible to collect the microorganisms contained in the sample by eliminating the constituents of the matrix of the latter. Such constituents may be dissolved salts, proteins, crystals, mucus, human cells, or the like.

A second objective of the invention is to provide a device for treating a biological sample which allows the rapid purification of a microbial content for subsequent analysis and also washing of the collecting filter or membrane.

A third objective of the invention is to provide a device for treating a biological sample which makes it possible both to concentrate microorganisms at the surface of the collecting filter or membrane and to resuspend the microorganisms thus concentrated, in a limited volume of buffer.

A fourth objective of the invention is to provide a device for treating a biological sample such that the steps of the treatment protocol using the device can be carried out in a totally automated manner by an appropriate automated pipetting device (e.g. Starlet from Hamilton Robotics), also called pipetting robot.

These objectives, among others, are achieved by means of the present invention which relates firstly to a device for preparing a biological sample comprising:
  a fixed support of which the base extends in a first plane,
  a filtration block that can be removable, said filtration block comprising a collecting tank that itself comprises a wall and a filtering means, the filtering means extending in a second plane and dividing said collecting tank into a collector area and a suction area, the suction area being designed to be connected to a suction means, the second plane of the filtering means being inclined relative to the plane of the base of the fixed support.

Alternatively, the present invention relates to a device for preparing a biological sample, comprising:
  a fixed support of which the base extends in a first plane,
  a filtration block that can be removable, said filtration block comprising a collecting tank that itself comprises a filtering means extending in a second plane and dividing said collecting tank into a collection area and a suction area, the suction area being designed to be connected to a suction means, the second plane of the filtering means being inclined relative to the plane of the base of the fixed support.

The term "biological sample" is intended to mean a liquid sample which may contain one or more constituents of interest, such as urine, blood cultures, sputum, cerebrospinal fluid, etc. These constituents of interest may be microorganisms such as yeasts or bacteria, or else microvesicles or exosomes.

Alternatively, a subject of the invention is a device for preparing a biological sample, comprising:
a fixed support of which the base extends in a first plane,
a filtration block that can be removable,
said filtration block comprising a collecting tank that itself comprises a filtering means extending in a second plane and dividing said collecting tank into a collection area and a suction area, the suction area being designed to be connected to a suction means, the second plane of the filtering means being inclined relative to the plane of the base of the fixed support; the filtration block also comprises a prefiltration tank that can be removable, said prefiltration tank comprising a filtering means dividing the prefiltration tank into a collection area and a suction area, the suction area of the prefiltration tank being in fluidic communication with the collection area of the collecting tank.

Alternatively, a subject of the invention is a device for preparing a biological sample, comprising:
a fixed support of which the base extends in a first plane,
a filtration block that can be removable,
said filtration block comprising a collecting tank that itself comprises a wall and a filtering means, the filtering means extending in a second plane and dividing said collecting tank into a collection area and a suction area, the suction area being designed to be connected to a suction means, the second plane of the filtering means being inclined relative to the plane of the base of the fixed support; the filtration block also comprises a prefiltration tank that can be removable, said prefiltration tank comprising a filtering means dividing the prefiltration tank into a collection area and a suction area, the suction area of the prefiltration tank being in fluidic communication with the collection area of the collecting tank.

Alternatively, the suction area of the prefiltration tank is designed to be connected to a second suction means.

Advantageously, the wall of the collecting tank in the collection area is partly inclined or in the shape of a pointed arch.

Advantageously, the wall of the collection area of the collecting tank is partly inclined or in the shape of a pointed arch.

Advantageously, the wall of the collecting tank in the collection area is rigid.

Advantageously, the filtering means of the collecting tank comprises at least one membrane with a pore size of between 0.02 and 1.5 µm, preferentially between 0.02 and 1 µm, more preferentially between 0.02 and 0.8 µm, even more preferentially between 0.02 µm and 0.45 µm.

Advantageously, the filtering means of the collecting tank comprises at least one membrane with a pore size of between 0.02 µm and 0.45 µm.

Advantageously, the filtering means of the prefiltration tank comprises at least one filter with a pore size of between 5 µm and 1000 µm, preferentially between 5 µm and 100 µm.

Alternatively, the filtering means of the prefiltration tank comprises a stack of filters.

Alternatively, the filtering means of the prefiltration tank comprises a stack of filters of increasing porosity from the suction area of the prefiltration tank to the collection area of the prefiltration tank. For this purpose, the filtering means of the prefiltration tank comprises or consists of a stack of prefilters of increasing porosity in order going from bottom to top, the prefilter placed at the top being the first to receive the liquid.

Advantageously, the second plane of the filtering means of the collecting tank is inclined relative to the plane of the base of the fixed support by an angle of between 10° and 60°, preferably between 20° and 50°, preferably between 25° and 45°, more preferentially equal to 30°.

Alternatively, the collecting tank comprises an upper part and a lower part which cooperate to hold the filtering means of the collecting tank.

Alternatively, the prefiltration tank comprises an upper part and a lower part which cooperate to hold the filtering means of the prefiltration tank.

Alternatively, the prefiltration tank comprises a means capable of cooperating with a tool for a pipetting robot, such as a pipette holder or a swab holder.

Alternatively, the filtration block also comprises a third filtration tank that can be removable, said third filtration tank comprising a filtering means dividing the third filtration tank into a collection area and a suction area, the collection area of the third filtration tank being in fluidic communication with the suction area of the collecting tank.

Advantageously, the suction means is a suction/discharge means.

The term "suction/discharge means" is intended to mean any means capable of causing a liquid to cross from the collection area of the collecting tank to the suction area of the collecting tank by suction and, optionally, from the suction area of the collecting tank to the collection area of the collecting tank by discharge. The advantage of the discharge is in particular that of being able to resuspend in a liquid a part of the concentrate of constituents of interest (also called retentate) derived from the biological sample by detaching it from the filtering means. A succession of suction and discharge steps also makes it possible to improve the concentration of the concentrate in the collection area, more particularly in a preferential area. This suction/discharge operation can therefore be carried out several times. This suction/discharge operation can be carried out by adding a buffer, for example a carbonate buffer or water, in particular for performing washing.

Advantageously, the second suction means which can be connected to the suction area of the prefiltration tank is a suction/discharge means.

Advantageously, the suction means is replaced with a means for placing the collecting tank and/or the prefiltration tank and/or the filtration tank at an increased pressure. The means for placing at an increased pressure is for that purpose designed to be connected to the collection area of the collecting tank and/or of the prefiltration tank and/or of the filtration tank. Advantageously, the second suction means is replaced by a second means for placing the collecting tank and/or the prefiltration tank at an increased pressure. The second means for placing at an increased pressure is for that purpose designed to be connected to the collection area of the collecting tank and/or the prefiltration tank.

Advantageously, the collecting tank and/or the prefiltration tank and/or the filtration tank is plugged by a plugging means. Even more advantageously, said plugging means is pierced by a tool for a pipetting robot, such as a pipette, a swab, a pipette holder, a swab holder, or a grasping tool such as tongs, or directly by the nozzle of a pipetting channel integrated into the robot.

Alternatively, said plugging means can be withdrawn by a tool for a pipetting robot, for example a grasping tool such as tongs, a pipette holder or a swab holder.

A subject of the invention is also the use of a device according to any one of the various embodiments presented, for treating a biological sample.

A subject of the invention is also a process for treating a biological sample using a device according to any one of the various embodiments presented, comprising the following steps:
- depositing the biological sample on the filtering means of the collecting tank,
- suctioning the biological sample through the filtering means of the collecting tank, using the suction means connected to the suction area of the collecting tank,
- collecting the microorganisms on the filtering means of the collecting tank.

Alternatively, a subject of the invention is a process for treating a biological sample using a device according to the invention, comprising the following steps:
- depositing the biological sample on the filtering means of the prefiltration tank,
- suctioning the biological sample through the filtering means of the prefiltration tank so as to deposit the biological sample on the filtering means of the collecting tank using the suction means connected to the suction area of the collecting tank,
- suctioning the biological sample through the filtering means of the collecting tank using the suction means connected to the suction area of the collecting tank,
- collecting the microorganisms on the filtering means of the collecting tank.

Alternatively, a subject of the invention is a process for treating a biological sample using a device according to the invention, comprising the following steps:
- depositing the biological sample on the filtering means of the prefiltration tank,
- suctioning the biological sample through the filtering means of the prefiltration tank so as to deposit the biological sample on the filtering means of the collecting tank using the second suction means connected to the suction area of the prefiltration tank,
- suctioning the biological sample through the filtering means of the collecting tank using the suction means connected to the suction area of the collecting tank,
- collecting the microorganisms on the filtering means of the collecting tank.

Alternatively, a subject of the invention is a process for treating a biological sample using a device according to the invention as described above, also comprising a step consisting in:
- discharging the biological sample through the filtering means of the collecting tank using the suction/discharge means connected to the suction area of the collecting tank.

Alternatively, a subject of the invention is a process for treating a biological sample using a device according to the invention as described above, for which the step consisting in:
- collecting the microorganisms on the filtering means of the collecting tank is replaced with a step consisting in:
- collecting the microorganisms on the filtering means of the collecting tank in a preferential collection area.

The device invented allows easy access to the filtering means of the collecting tank, for example to the membrane, in order to be able to perform washing or to collect the microorganisms, for example by resuspending with a pipette or by swabbing.

The incline of the second plane in which the filtering means of the collecting tank extends relative to the plane of the base of the fixed support can be obtained by means of the geometry of the fixed support on which the filtration block is placed and/or by inclination of the filtering means. By way of example, the fixed support may comprise a plane that is inclined relative to its base, said base being horizontal, the filtration block being placed on this inclined plane and the filtering means of the collecting tank extending in a plane parallel to this inclined plane.

By virtue of this incline, when the liquid is dispensed, originating from the filtering means of the prefiltration tank and/or directly on the filtering means and/or by suction/discharge, it naturally flows on the filtering means, where it can optionally be again suctioned, in a preferential collection area.

The incline of the second plane in which the filtering means of the collecting tank extends relative to the plane of the base of the fixed support is fixed throughout the filtration step. The shape of the wall of the collecting tank makes it possible, in cooperation with the incline of the second plane in which the filtering means extends, to promote retention of the biological sample in a preferential collection area when said sample is dispensed in the collecting tank. This preferential area corresponds to the bottom part of the filtering means. This preferential area contains, following a filtration step, the majority of the concentrate of microorganisms or of constituents of interest present in the biological sample. The suction area is therefore defined by the second plane of the filtering means and the wall of the collecting tank such that the filtering means and the wall of the collecting tank are in contact in the preferential area. The advantage of this contact is that it prevents the formation of dead volumes where a liquid portion of the biological sample could stagnate after the filtration step. Another advantage of this contact and of this preferential area is that of promoting retention of the biological sample in a delimited and predictable area, thereby promoting a higher yield of recovery by a pipetting robot automated device which does not have a vision system, in particular a vision system intended to locate a bacterial layer on the surface of the filtering means. The geometry of this preferential area can be modified according to the angle formed between the filtering means and the wall of the collecting tank. This angle may be closed (acute) so as to create a localized preferential area, but deep or open (obtuse) so as to limit the depth of the preferential area while at the same time increasing the surface area covered by said area for the same volume of liquid contained in this area. The angle formed between the filtering means and the wall of the collecting tank in the preferential area is thus between 10 and 170 degrees, preferentially between 30 and 150 degrees, preferentially between 50 and 130 degrees, preferentially between 70 and 120 degrees, more preferentially between 80 and 100 degrees, more preferentially between 50 and 70 degrees. Even more preferentially, the angle is 90 degrees. Even more preferentially, the angle is 60 degrees.

Preferentially, the filtering means and the wall of the collecting tank are in contact over the entire surface area of the filtering means. The advantage of this contact over the entire surface area of the filtering means is to limit the adhesion to the wall of any debris contained in the biological sample and to simplify the process of filtration of the biological sample, it being possible for said sample to be distributed anywhere in the collection area of the collecting tank, in particular on the wall or directly on the filtering means.

As the jets of collecting buffer are delivered, the microorganisms concentrate toward the bottom part of the filtering means forming, for example, a closed angle with the wall of the collecting tank. A bacterial concentrate can, for example, be recovered without significant loss of volume (volume recovered from 300 to 700 µl), relative to the volume of collecting buffer dispensed (volume 400 to 1000 μl), i.e. a factor of 10 to 20 relative to the initial volume of biological sample. The incline of the second plane of the filtering means relative to the plane of the base of the fixed support can be between 10° and 60°, preferably between 20° and 50°, preferably between 25° and 45°, more preferentially equal to 30°.

The device according to the invention can be readily used with an automated pipette, also called pipetting robot. For this purpose, the wall of the collecting tank is designed so as to be able to vertically present a tool for a pipetting robot, such as a pipette or a swab, in line with the entire surface of the filtering means of the collecting tank directly after or during the filtration step. The advantage is that of not having to move the device, the collecting tank and/or the filtering means in order to collect the concentrate of constituents of interest. Another advantage is that of being able to collect, by abrasion or detachment, the concentrate of constituents of interest, such as microorganisms, deposited on all or part of the filtering means, after filtration, by means of a swab. This geometry also facilitates the manual and/or automatic pipetting and/or swabbing operations, in particularly directly after or during the filtration step. Thus, the shape of the wall of the collecting tank is designed so that an operator or a pipetting robot can have access to the entire surface area of the filtering means of the collecting tank, in particular vertically with respect to said filtering means. A pipetting robot in fact has a pipette which moves translationally according to three degrees of freedom and which does not make it possible to make complex movements or to present a pipette other than vertically.

This access to the entire surface area of the filtering means of the collecting tank thus makes it possible to dispense a liquid on an area of the filtering means of the collecting tank with a powerful jet and then to suction this same liquid in order to be able to powerfully redispense it on another area of the filtering means of the collecting tank. A series of about twenty dispensing/resuctioning operations can thus be carried out in order to concentrate and then harvest the constituents of interest retained on the entire surface area of the filtering means of the collecting tank. The incline of the collecting tank additionally allows the collection liquid to localize in the preferential collecting area while limiting the losses of volume that would be created by a horizontal filtration system.

Advantageously, the wall of the collecting tank can have at least one part which is inclined, or in the shape of a pointed arch, designed to be able to vertically present a pipette, in line with the concentrate of constituents of interest, in particular of microorganisms, the concentrate being predominantly located in the preferential area. This geometry also facilitates the manual and/or automatic pipetting and/or swabbing operations, in particular by preventing striking of the wall of the collecting tank.

The advantage of such a device is that it can be used, on the same type of device, for various types of biological samples (urine, blood cultures, etc) of different volumes (10 ml to 1 ml), by selecting a treatment protocol suitable for the biological sample under consideration. Thus, for blood cultures, the protocol is a selective lysis followed by a single filtration on a filtering means, for example a membrane. For clinical urine, the protocol consists of a prefiltration on the filtering means of the prefiltration tank, followed by a filtration on the filtering means of the collecting tank, for example on a membrane. The two protocols can advantageously be followed by one or more steps of washing the bacterial concentrate using suitable washing solutions.

Moreover, for an approach consisting of Identification Typing Resistance Virulence (ITRV) of microorganisms, such as bacteria, by means of Electrospray ionization (ESI) mass spectrometry technology, having microorganisms in liquid suspension is more practical for the rest of the protocol (lysis followed by extraction of proteins or lysis followed by tryptic digestion of proteins).

The advantage of such a device is also that it can be disposable. Since the materials used to produce it are inexpensive, the device and/or the filtration block and/or the prefiltration tank can be disposable for the treatment of a sample. Even more advantageously, the filtration block is removable. Even more advantageously, the filtration block is removable and disposable.

The prefiltration tank can also be removable. Advantageously, the prefiltration tank is removable and disposable.

The device can also be used with a view to the automatic preparation of MALDI-TOF plates after extraction of the microorganisms from the biological samples. The microorganisms can, for example, be collected directly on the filtering means of the collecting tank by means of a robotic tool so as to be deposited on a MALDI-TOF plate or to be used in the preparation of a concentrated and calibrated suspension of microorganisms. In the same way, the microorganisms can be deposited in a liquid suspension that will be centrifuged in order to be able to recover a microorganism pellet. This microorganism pellet will then be deposited on a MALDI-TOF plate.

BRIEF DESCRIPTION OF THE DRAWINGS

The purposes and advantages of the device according to the present invention will be understood more clearly in the light of the following examples which are in no way limiting, with reference to the drawing, in which:

FIG. 18 illustrates an experiment using the device according to the invention for the treatment of samples of inoculated blood cultures.

DETAILED DESCRIPTION

According to a first embodiment, the collecting tank is accessible without having to remove the prefiltration tank. The device according to the invention can thus be placed in a pipetting robot, which would pour the biological sample into the prefiltration tank if a prefiltration is required, or into the collecting tank if a filtration is sufficient. Such a device is therefore capable of treating biological samples of various nature, such as urine or blood, without having to manipulate the prefiltration tank. When the prefiltration tank is not removed from the device, the suction area of the prefiltration tank is in fluidic communication with the collection area of the collecting tank.

Figure 1:
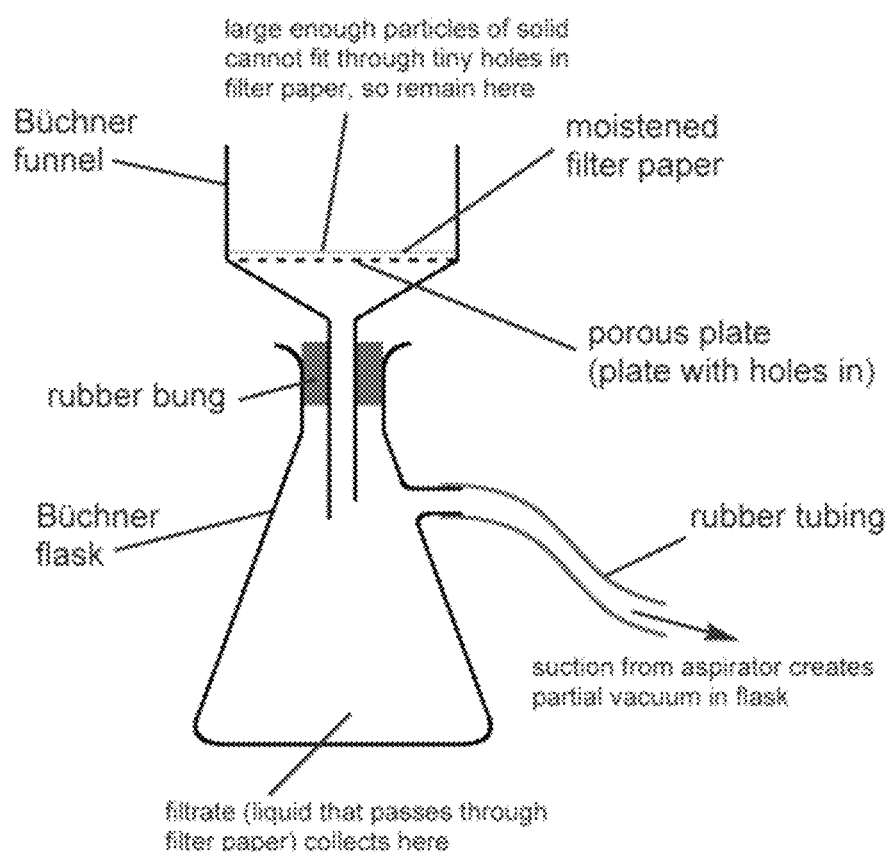
FIG. 1 is a prior art device.
Figure 2:
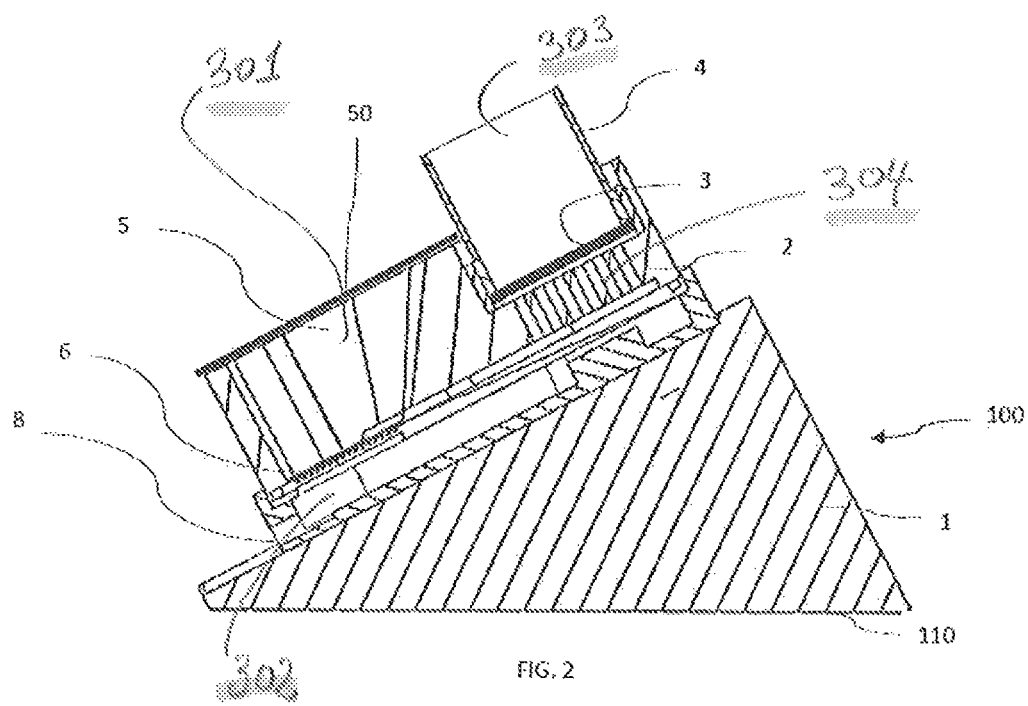
FIG. 2 is a sectional diagrammatic representation of a first embodiment of the device according to the invention comprising a filtration block on a fixed support inclined at 30°.
Figure 3:
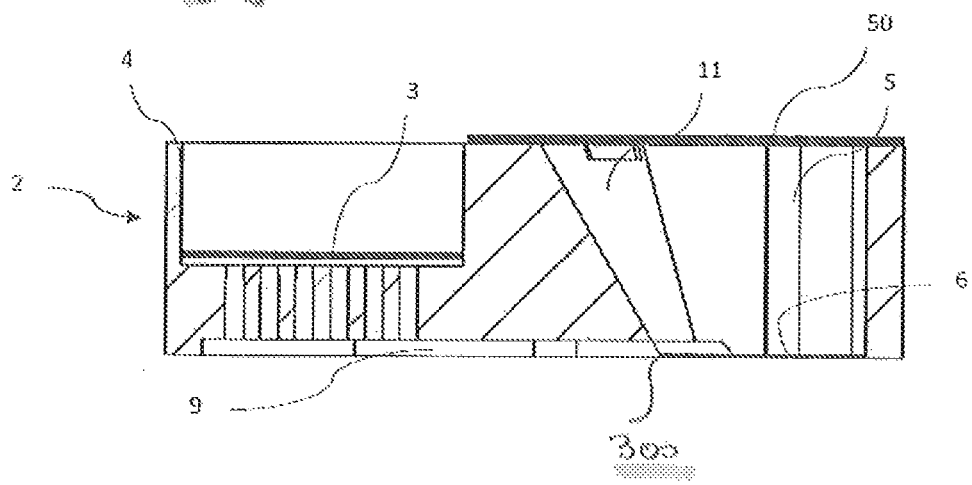
FIG. 3 is a sectional diagrammatic representation of the filtration block, according to the first embodiment.

With reference to FIGS. 2 and 3, the device 100 is composed of a fixed support 1 inclined at 30°, on which is placed a filtration block 2 that can be removable. The filtration block 2 comprises a filtering means, also called prefilter, or a stack of prefilters 3, contained in a prefiltration tank 4 and which makes it possible to clarify the solutions to be filtered without retaining the microorganisms. The filtration block also comprises a collecting tank 5 with a filtering means, for example a membrane 6 placed at the bottom of the tank. Alternatively, the angle of 30° between the plane in which the filtering means of the collecting tank extends and the plane of the base 110 of the fixed support 1 is obtained by inclining the fixed support 1 and/or the filtration block 2 and/or the membrane 6. Alternatively, the collecting tank 5 has at least one wall of which at least one part is inclined, 11. The collecting tank 5 is plugged by a plugging means. This plugging means consists, for example, of a plugging film 50, as represented in FIG. 2. This plugging film makes it possible maintain a low-pressure state downstream of the prefilter(s) during the operation of filtration of complex media such as urine. The plugging film 50 may be a self-adhesive film in particular of biaxially oriented polypropylene (BOPP), polyethylene terephthalate (PET), polyester (PE), or aluminum/PE type. Such a self-adhesive film can be easily detached by an operator or by means of an automated device. Alternatively, the film can be welded onto the filtration block 2, by any appropriate means (ultrasonic welding, thermosealing, etc). Such a film is then pierced by an appropriate tool, which can cooperate with the tool holder of an automated device. Advantageously, an appropriate tool is a tool for a pipetting robot, such as a pipette holder, a swab holder, a grasping tool such as tongs or directly the nozzle of a pipetting channel integrated into the robot.

Advantageously, the device and/or the filtration block and/or the prefiltration tank can be disposable. Even more advantageously, the filtration block is removable. Even more advantageously, the filtration block is removable and disposable.

The prefiltration tank can also be removable. Advantageously, the prefiltration tank is removable and disposable.

According to one alternative, the plugging means can consist of a part of plastic cap type comprising an appropriate opening mechanism, making it possible to provide the required leaktightness when it is placed on the collecting tank 5, so as to generate the low-pressure state while at the same time enabling, when it is raised, the possibility of having access to the collecting tank.

Figure 4:
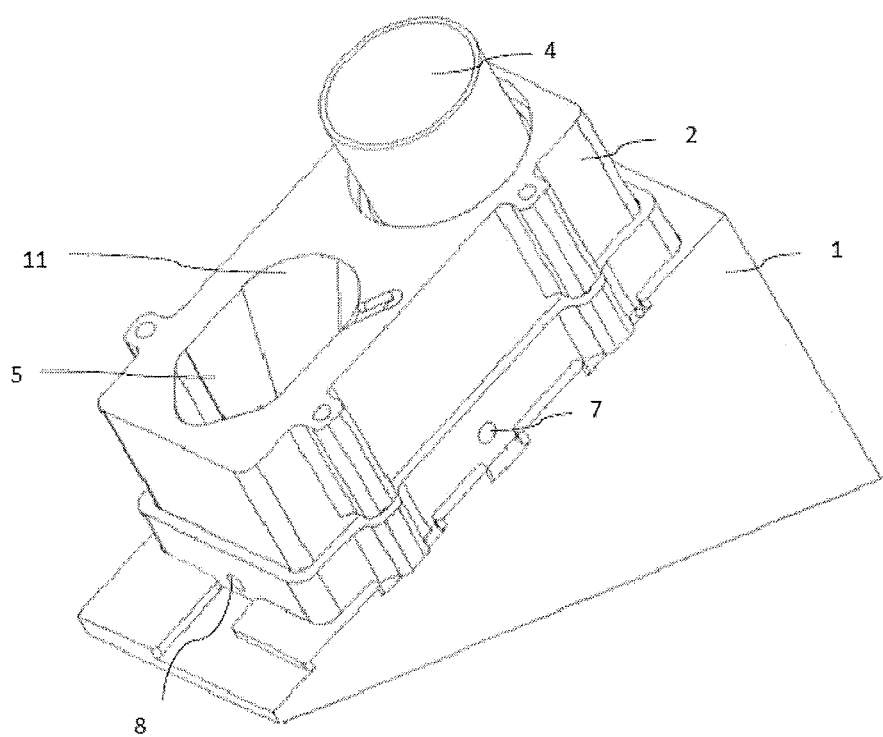
FIG. 4 is a diagrammatic representation, in perspective, of the first embodiment of the device according to the invention.

With reference to FIG. 4, the device is connected to a vacuum suction system (for example a pump), not represented, and a waste tank which collects the filtered liquids. The suctioning is carried out through the suction orifices of the prefilter 7 and of the membrane 8, located on the fixed support 1.

The leaktightness between the filtration block 2 and the fixed support 1 can be obtained by any appropriate means. In the embodiment presented, the filtration block 2 is screwed onto the fixed support 1 and a seal, not represented, is placed between the filtration block 2 and the fixed support 1.

A valve, not represented, makes it possible to manage the protocol by suctioning either at the level of the prefilter 3, or at the level of the membrane 6 (that is to say with continuous suction downstream of the membrane and alternating suction downstream of the prefilter). The valve can be integrated into the vacuum suction system or can be an integral part of the filtration device.

Figure 5:
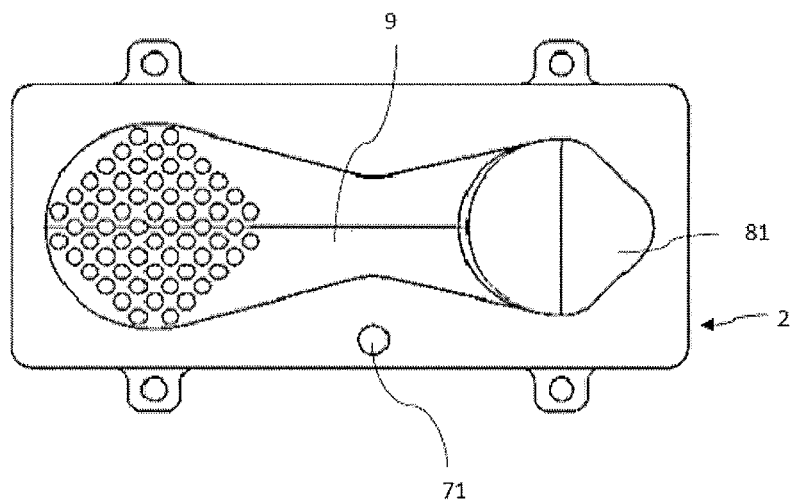
FIG. 5 is a diagrammatic representation, viewed from below, of the filtration block according to the first embodiment.
Figure 7:
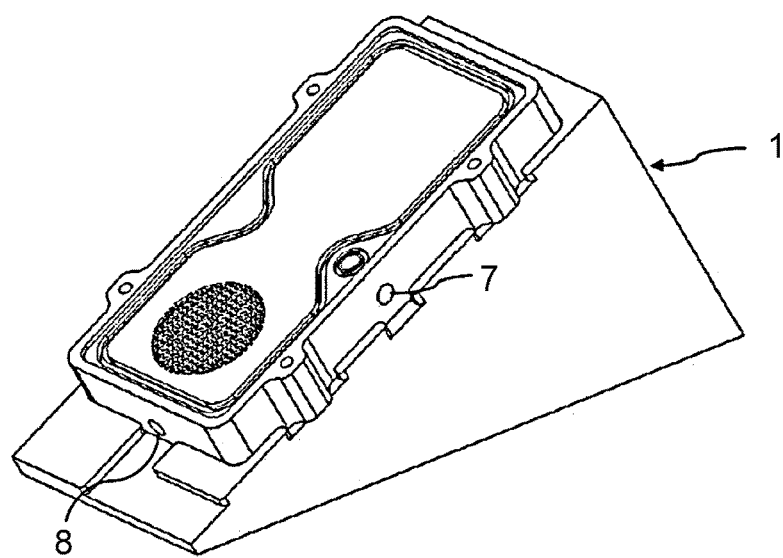
FIG. 7 is a diagrammatic representation, in perspective, of the fixed support inclined at 30°, according to the first embodiment.

As represented in FIGS. 5 and 7, the filtration block 2 can be removable. In this case, the suction orifice of the prefilter 7 is in fluidic communication with the suction area of the prefiltration tank 4 by means of an orifice 71 on the filtration block 2 when the latter is placed on the fixed support 1. Likewise, when the filtration block 2 is placed on the fixed support 1, the suction orifice 8 of the membrane communicates with the emerging part 81 of the collecting tank 5, itself in fluidic communication with the suction area of the collecting tank 5.

Figure 6:
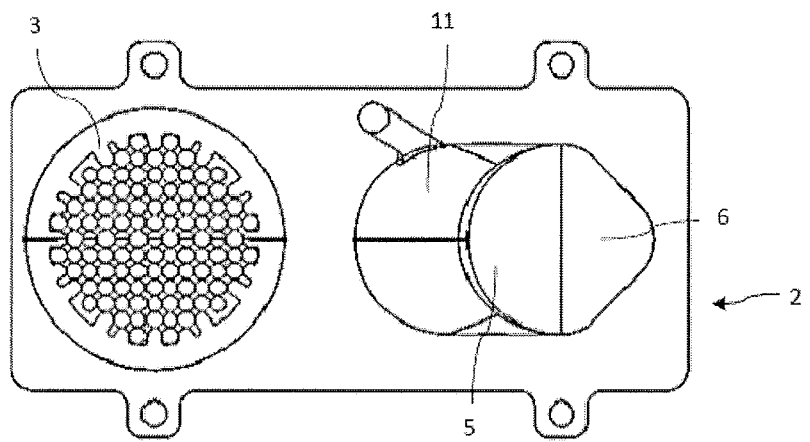
FIG. 6 is a diagrammatic representation, viewed from above, of the filtration block according to the first embodiment.

With reference to FIG. 6, it is noted that the collecting tank 5 has at least one wall of which at least one part 11 is inclined.

In order to carry out a step of prefiltration of a sample using the first embodiment of the device according to the invention and with reference to FIGS. 4 and 5, a valve, not represented, makes it possible to manage the protocol by suctioning either downstream of the prefilter 3, or downstream of the membrane (that is to say with continuous suction downstream of the membrane and alternating suction downstream of the prefilter).

The liquid to be treated, for example urine, is pipetted into the prefiltration tank 4 above the prefilter 3. The vacuum pump is turned on. The valve is adjusted to suction through the prefilter 3 by means of the suction orifice of the prefilter 7 and, where appropriate, the orifice 71. Once the liquid has been prefiltered, it is directed naturally by the geometry of the device and stored above the microorganism-retaining membrane 6. The prefiltered liquid thus passes through an intermediate tank 9, placed between the prefilter 3 and the collecting tank 5, as represented in FIG. 5.

In order to carry out a step of filtration of a sample on the membrane 6 and with reference to FIGS. 4 and 5, the valve is adjusted to suction at the level of said membrane 6 by means of the membrane suction orifice 8 and, where appropriate, the emerging part 81 of the collecting tank 5. The microorganisms are collected on this membrane 6. The pore size of this membrane is less than the diameter of the microorganisms to be collected. Preferentially, the pore size is between 0.22 and 0.45 μm. The membrane can be washed in order to purify the microorganisms. Advantageously, the wall of the collecting tank 5 comprises at least one inclined part 11 or at least one part in the shape of a pointed arch. This shape of the wall makes it possible, in cooperation with the incline of the membrane 6, to promote retention of the microorganisms in a preferential area, corresponding to the bottom part of the filtering means 3. This part then forms an acute angle between the filtering means 3 and the wall of the collecting tank 5. Thus, in a subsequent step of recovery of the microorganisms, resuspension in a reduced volume of liquid can be more easily carried out, in particular automatically. The accessibility to this area is also improved. Advantageously, this retention of the microorganisms in a preferential area makes it possible to localize the microorganisms in a delimited and predictable area, thereby promoting a higher yield of recovery by an automated device which does not have a vision system intended to locate a bacterial layer on the surface of the membrane.

Figure 8:
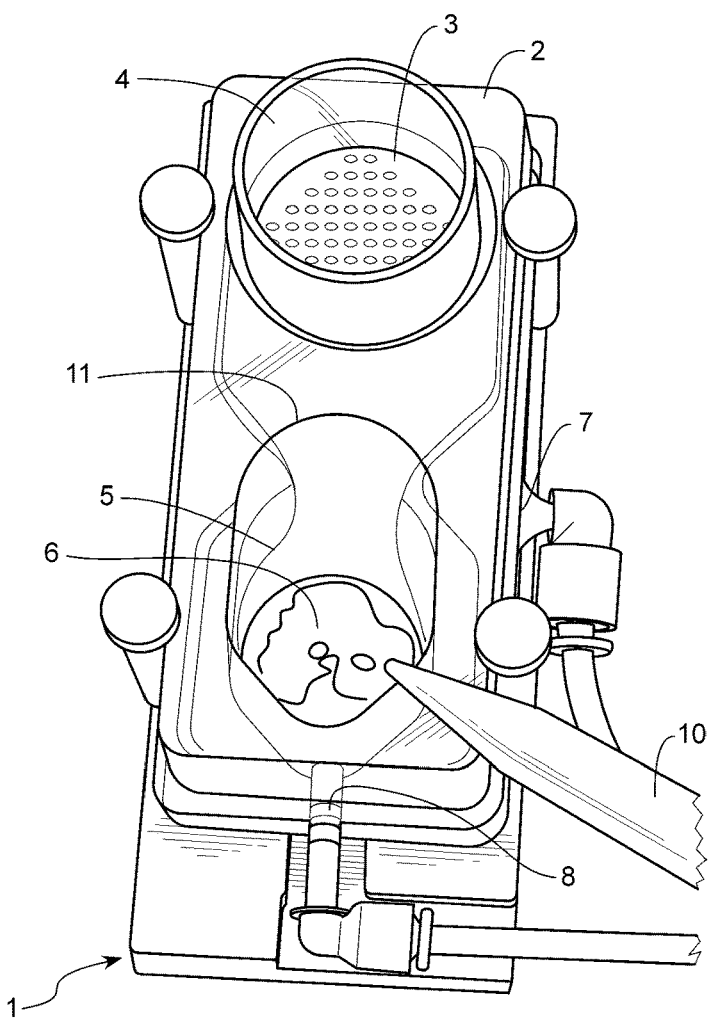
FIG. 8 is a photograph of the first embodiment of the device according to the invention.

Following this step of filtration on the membrane 6 and with reference to FIG. 8, the vacuum pump is turned off in order to bring the pressure downstream of the membrane 6 back to atmospheric pressure. The microorganisms then adhere to the membrane 6 and can be recovered/collected in different ways, and in a nonlimiting manner:

- by resuspending using the pipette 10 with a liquid by dispensing the latter on an area of the membrane with a powerful jet and then by suctioning this same liquid in order to be able to powerfully redispense it on another area of the membrane. A series of about twenty dispensing/resuctioning operations is carried out in order to harvest the bacteria retained on all the areas of the membrane. The incline of the collecting tank allows the collection liquid to become localized in the preferential collection area while limiting the losses of volume that a horizontal filtration system would generate (rapid ejection of a liquid, for example a neutral buffer or solvent), see FIG. 8. For this purpose, the collecting tank 5 advantageously has at least one wall of which at least one part 11 is inclined so as to allow the vertically presented pipette 10 to come and remove the microorganisms collected on the entire surface area of the membrane 6, without striking the wall of the collecting tank 5;
- by swabbing the surface of the membrane 6: either with a swab alone, or with a device combining a pipetting tip comprising a swab at its end. Such a device comprises a pipetting tip, the end of which that opens out and suctions the liquid, is wrapped with the porous part of a swab. The advantage of such a device is that it can suction the liquid by means of the pipetting tip, through the porous part of the swab, and then come into contact with the membrane, or with any filtering means of the collecting tank, in order to "detach" the concentrate of microorganisms by abrasion, this operation being impossible to carry out with the conventional end of a pipetting tip;
- by directly recovering the membrane 6 then resuspending in a tube or directly lyzing the microorganisms. The membrane 6 is therefore removably mounted in the collecting tank 5;
- by rinsing: arrival of the liquid via the back face of the membrane 6, the back face of the membrane being the face directed facing the suction orifice 8 of the membrane and, where appropriate, the emerging part 81 of the collecting tank 5. Alternatively, the liquid (neutral buffer, buffer containing detergents or solvent) is deposited on the membrane 6 in the collecting tank 5, suctioned, and then discharged via the back face of the membrane 6. This suction/discharge operation can be carried out several times.

The various recovery/collection methods may be adjusted according to the microorganisms sought or the type of sample. Indeed, some microorganism concentrates exhibit a very strong adhesion to the membrane. It is then impossible to collect the microorganisms by rapid ejection of a liquid, the liquid jet not being sufficiently powerful to detach the concentrate. Only an abrasion technique (using a swab or a pipetting tip wrapped with the porous part of a swab at its end) is then effective for detaching the concentrate from the membrane.

Figure 9:
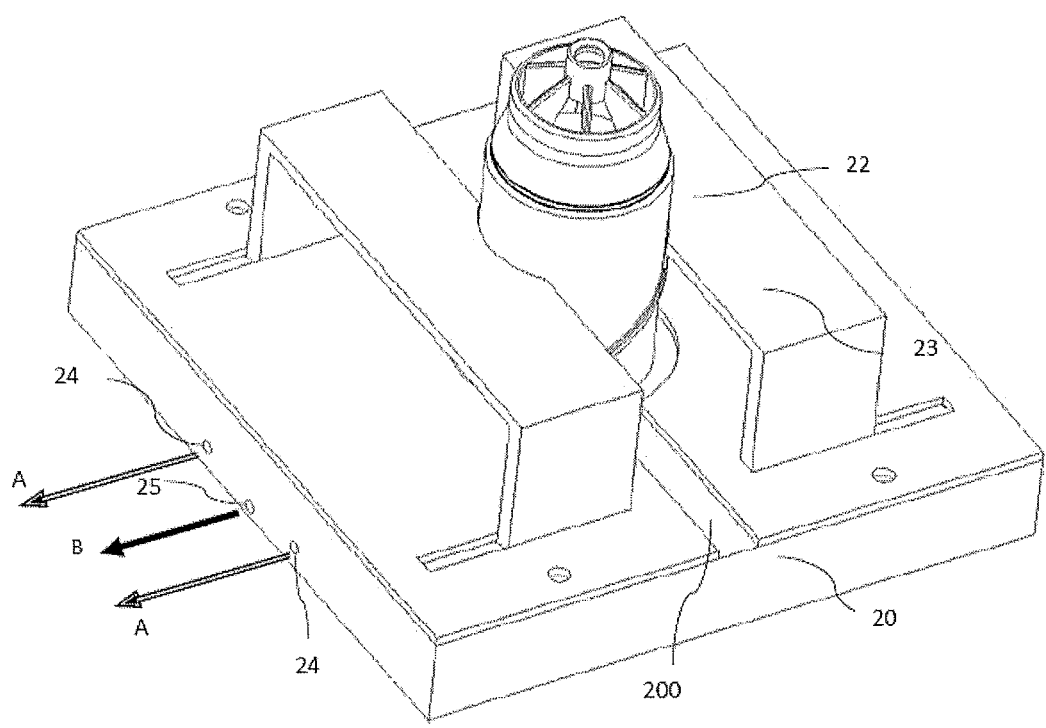
FIG. 9 is a diagrammatic representation, in perspective, of a second embodiment of the device comprising a support with a slide.

A second embodiment is illustrated in FIG. 9. In this embodiment, the prefiltration tank must be removed in order to have access to the collecting tank. The prefiltration tank is, for example, stacked on the collecting tank. Such a device is therefore capable of treating biological samples of various natures, such as urine or blood, while at the same time being compact. When the prefiltration tank is not removed from the device, the suction area of the prefiltration tank is in fluidic communication with the collection area of the collecting tank.

In this embodiment, the device is composed of a fixed support 20 on which is placed a filtration block 22 that can be removable. In the embodiment presented, the filtration block 22 is held on the support 20 by means of two slides 23. The device is connected to a vacuum suction system (for example a pump), not represented, and a waste tank which collects the filtered liquids. The suctioning is carried out through the prefilter suction orifices 24 and the membrane suction orifice 25, which are located on the fixed support 20. The fixed support 20 thus comprises several suction orifices forming two suction circuits marked by the arrows "A" and "B". The two suction circuits thus make it possible to suction downstream of the membrane and/or downstream of the prefilter independently, by means of the suction areas of the collecting tank and of the prefiltration tank. Alternatively, if the suction is sufficient downstream of the membrane, the device can be held on the support without the use of slides.

The leaktightness between the filtration block 22 and the fixed support 20 can be obtained by any means. In the embodiment presented, the filtration block 22 is held on the fixed support 20 and two O-ring seals, not represented, are placed between the filtration block 22 and the fixed support 20 in order to seal the "suction A" and "suction B" suction circuits.

Figure 10:
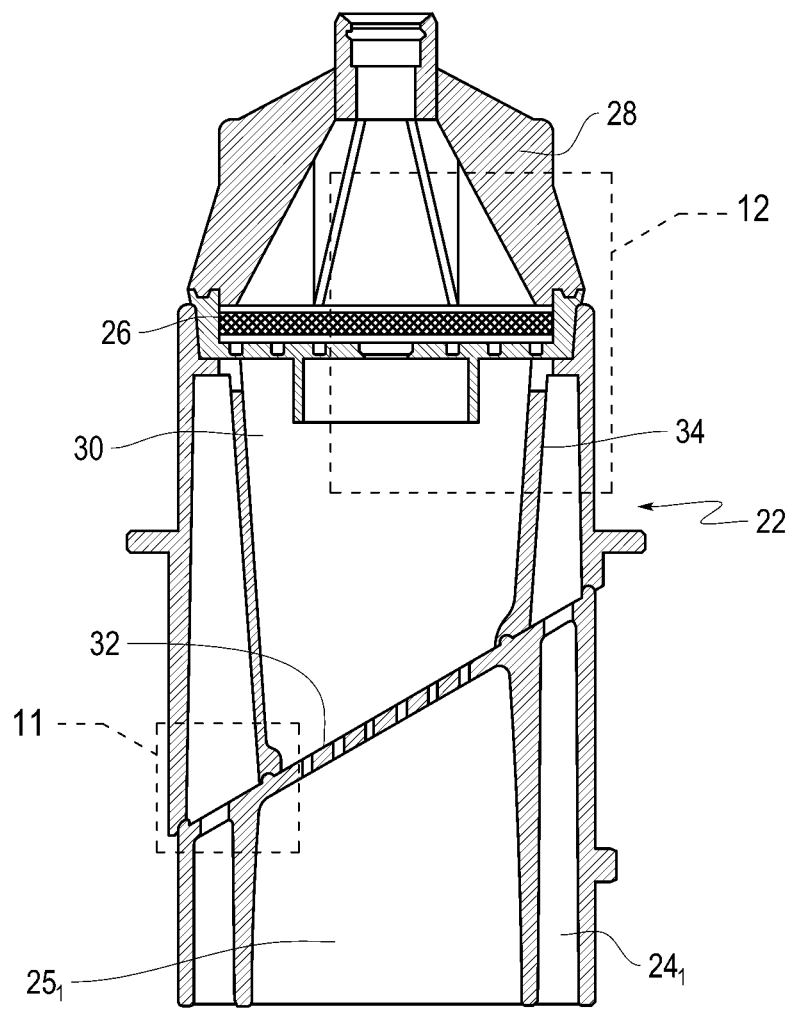
FIG. 10 is a sectional diagrammatic representation of the second embodiment of the device.

With reference to FIG. 10, the filtration block 22 comprises a filtering means, also called prefilter or prefilter stack 26, contained in a prefiltration tank 28 and which makes it possible to clarify the solutions to be filtered without retaining the microorganisms. The filtration block 22 also comprises a collecting tank 30, and a filtering means, for example a membrane 32, placed at the bottom of the collecting tank 30. The membrane 32 is inclined by an angle of 30° relative to the plane formed by the base 200 of the fixed support 20, that is to say 60° relative to the vertical.

Alternatively, the collecting tank 30 has at least one wall of which at least one part 34 is inclined or in the shape of a pointed arch.

Since the filtration block 22 can be removable, the prefilter suction orifice 24 then cooperates with an orifice 24₁ on the filtration block 22. Likewise, the membrane suction orifice 25 cooperates with the emerging part of the collecting tank 25₁.

A valve, not represented (optionally integrated into the device), makes it possible to manage the protocol by suctioning either downstream of the prefilter 26, or downstream of the membrane 32 (i.e. with continuous suction downstream of the membrane 32 and alternating suction downstream of the prefilter 26).

Figure 11:
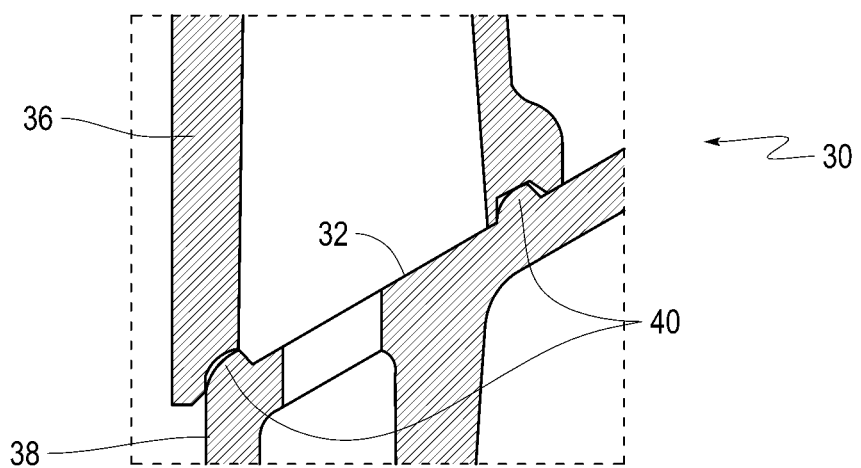
FIG. 11 is a sectional diagrammatic representation of Detail A of the second embodiment of the device, as represented in FIG. 10.

With reference to FIG. 11 corresponding to Detail A, the collecting tank 30 can be made of two assembled parts 36 and 38. In this embodiment, the upper part 36 and the lower part 38 cooperate in order to hold the membrane 32 in position, for example by means of two lugs 40. Advantageously, the two parts 36 and 38 are welded in order to hold the membrane.

Figure 12:
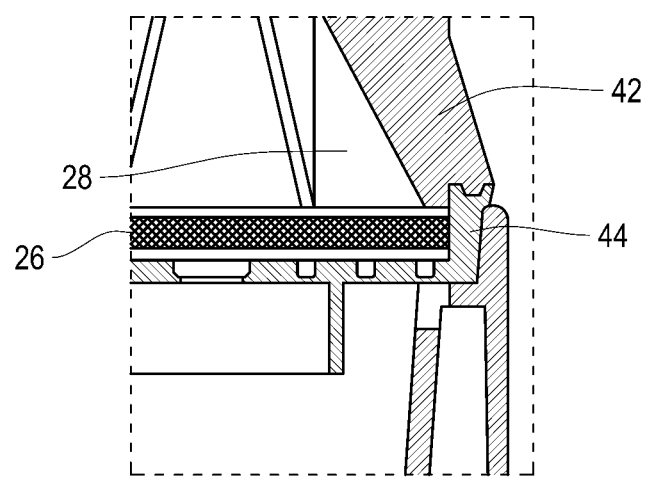
FIG. 12 is a sectional diagrammatic representation of Detail B of the second embodiment of the device, as represented in FIG. 10.
Figure 14:
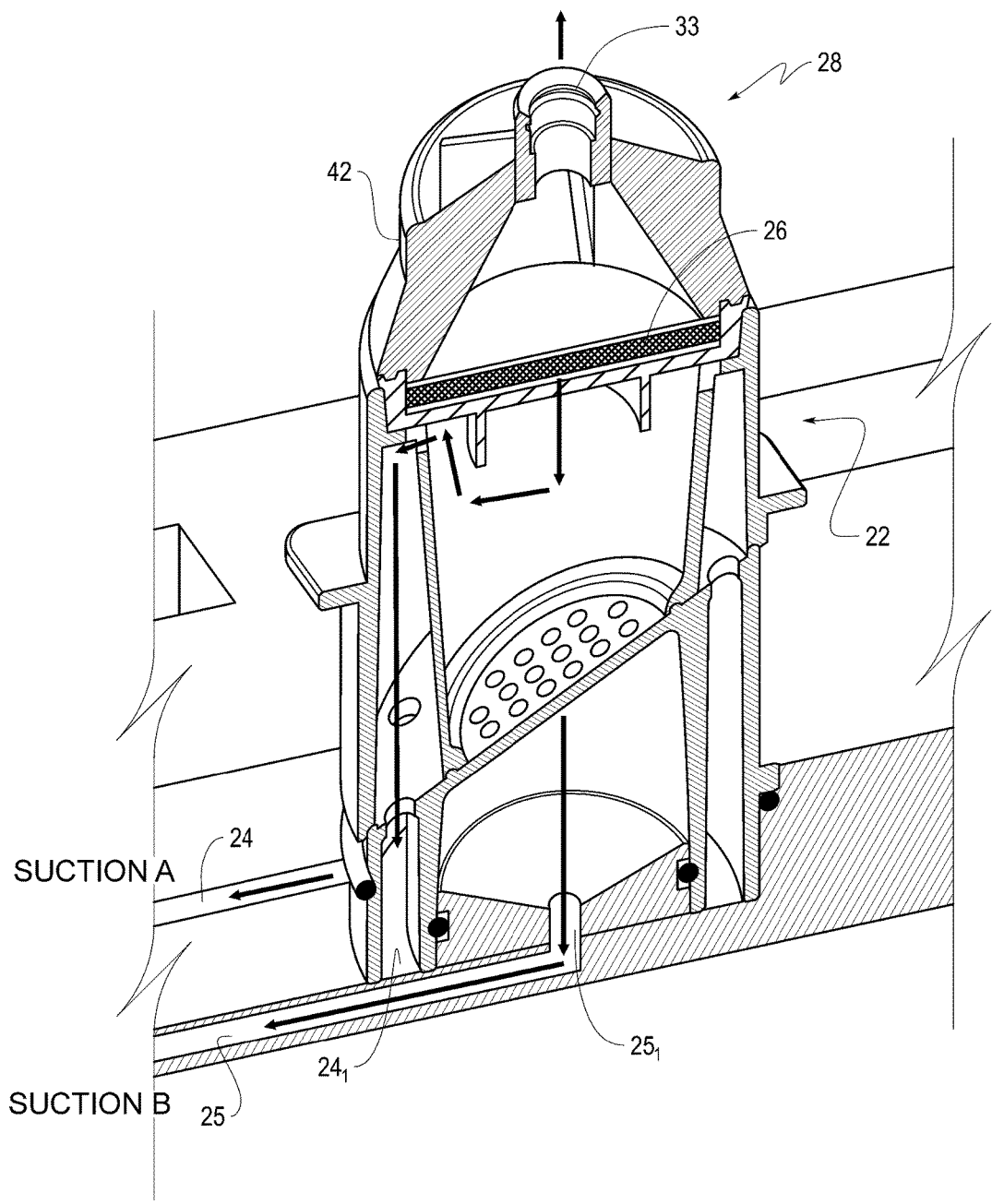
FIG. 14 is a diagrammatic representation, in perspective and in section, of the second embodiment of the device exhibiting the suction flows "A" and "B".

With reference to FIG. 12 corresponding to Detail B, the prefiltration tank 28 can be made of two assembled parts, an upper part 42 and a lower part 44 which serve as a support for the prefilter 26. In this embodiment, the upper part 42 and the prefilter support 44 cooperate so as to hold the prefilter 26 in position. Advantageously and as represented in FIG. 14, the upper part 42 comprises a means 33 capable of cooperating with a pipette-hold tool of a pipetting robot. The means 33 may also assume an appropriate form (for example one or more orifice(s) or lug(s)) making it possible to be manipulated automatically by a mechanical element (such as tongs), a grasping tool for a pipetting robot, a pipette holder, or a swab holder, or directly by the nozzle of a pipetting channel integrated into the robot. Advantageously, this means 33 may comprise a cylindrical part into which the pipette-holder tool can be inserted and be held so as to raise the prefiltration tank 28 and thus reveal access to the membrane 32. In one particular embodiment, this cylindrical part is held by a set of ribs arranged radially on the cylindrical part so as to define at least one means of access to the prefilter or to the prefilter stack 26. This means of access allows an apparatus such as a pipetting robot to present a tool vertically to the prefilter or to the prefilter stack so as to dispense a liquid (e.g. the sample to be treated) therein, this being without manipulating or striking the upper part 42.

Figure 13:
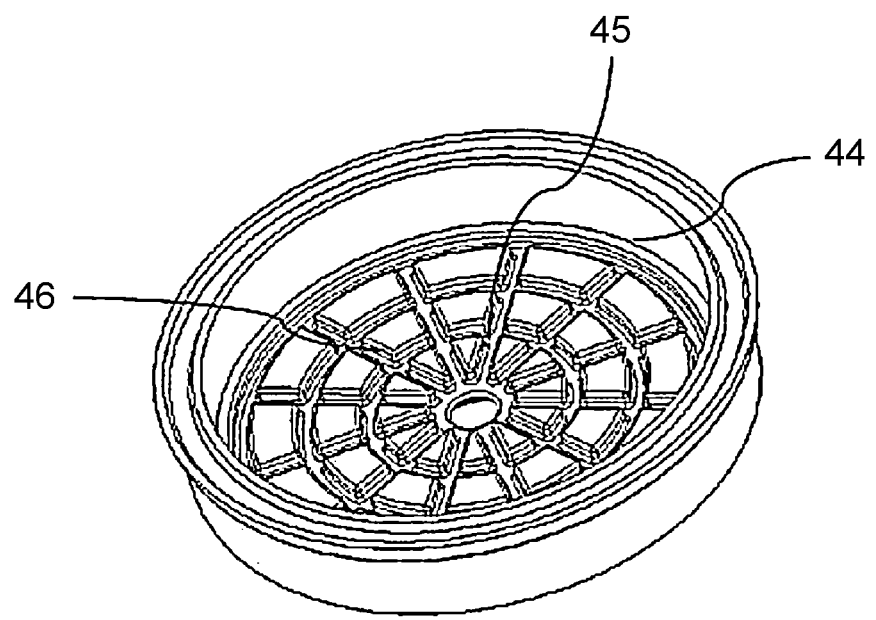
FIG. 13 is a diagrammatic representation, in perspective, of the prefilter support of the second embodiment of the device.

With reference to FIG. 13, the prefilter support 44 can have projections 46 extending radially relative to the suction orifice 45 of the prefilter support 44. The projections 46 are arranged on the face opposite the prefilter, in order to hold the prefilter in position while at the same time facilitating the flow of the filtrate. Advantageously, the projections 46 extend radially relative to the suction orifice 45 and according to one or more concentric circle(s) of which the center is the suction orifice 45. The prefilter support 44 makes it possible both to support the prefilter or the prefilter stack 26 and to seal the collecting tank when this tank is placed under vacuum, thus allowing effective passage of the sample through the prefilter or the prefilter stack 26.

With reference to FIG. 14, a protocol for filtering a urine sample using the second embodiment of the device comprises the following steps:

1ˢᵗ step: Pouring the urine onto the prefilter 26. In the case of an automated protocol, the urine can be poured by a pipetting robot which comes to position itself vertically to the prefilter 26 through the means of access to the prefilter of the upper part 42. Alternatively, the urine can be poured, manually or automatically, directly onto the prefilter 26 in the case where the upper part 42 is not present.

2ⁿᵈ step: Activating the suction "A" by means of the suction orifices 24 and 24₁. The urine passes through the prefilter 26 and is deposited on the membrane 32.

3ʳᵈ step: Activating the suction "B" by means of the suction orifices 25 and 25₁. The microorganisms remain on the membrane 32 while the "waste" is suctioned to the waste tank.

4ᵗʰ step: Removing the prefiltration tank 28 in order to gain access to the membrane 32, for example using an automated means such as robot tool used to manipulate pipettes, 5ᵗʰ step: Optionally carrying out one or more steps of washing the membrane and the microorganisms by distributing volumes of buffer with a (manual or automated) pipette.

6ᵗʰ step: Recovering the microorganisms. The microorganisms are then concentrated by the force of gravity and the action of the suction in the bottom part of the slope formed by the membrane 32 and the wall of the collecting tank 30, said wall advantageously comprising an inclined shape 34 or the shape of a pointed arch. The microorganisms are then concentrated in a delimited area, corresponding to the preferential collection area, so as to allow the recovery of the microorganisms by an automatic pipetting robot in a reduced volume of liquid.

The step of recovery/collection of microorganisms on the membrane 32 can be carried out by the same means as those stated for the first embodiment of the device according to the invention.

Figure 15:
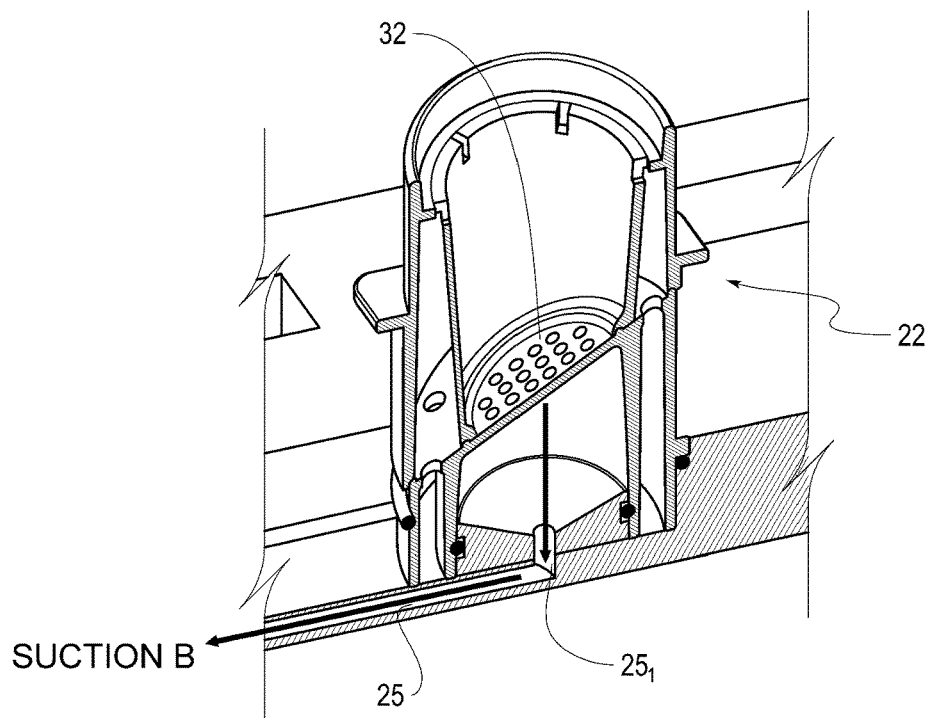
FIG. 15 is a diagrammatic representation, in perspective and in section, of the second embodiment of the device without the prefiltration stage, exhibiting the suction flow "B" in this use.

With reference to FIG. 15, a protocol for filtering a previously lyzed blood sample, using the second embodiment of the device, without the prefiltration tank 28, comprises the following steps:

1ˢᵗ step: Pouring the previously lyzed blood onto the membrane 32.

2ⁿᵈ step: Activating the suction "B" by means of the suction orifices 25 and 25₁. The microorganisms remain on the membrane 32 while the "waste" is suctioned to the waste tank.

3ʳᵈ step: Optionally carrying out one or more steps of washing the membrane and the microorganisms by distributing the volumes of buffer using a (manual or automated) pipette.

4ᵗʰ step: Recovering the microorganisms.

Figure 16:
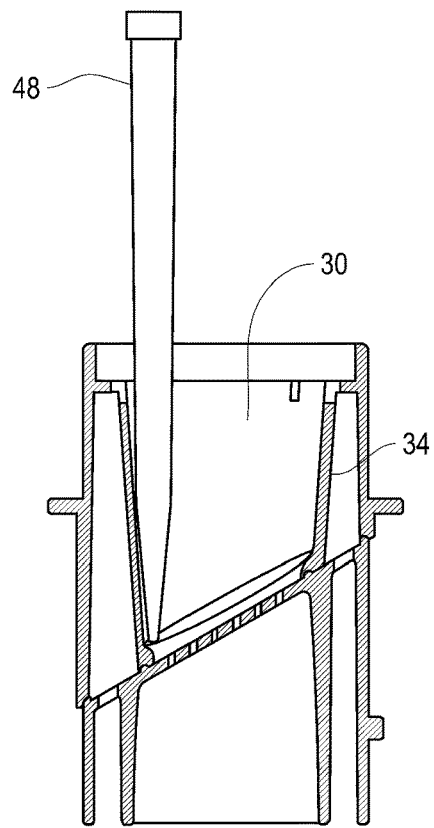
FIG. 16 is a sectional diagrammatic representation of the second embodiment of the device without the prefiltration stage, combined with a pipetting device.

With reference to FIG. 16, the recovering of the microorganisms can be carried out by resuspending using the pipette 48 with a liquid (rapid ejection of the liquid, for example a neutral buffer, buffer with detergents or solvent). For this purpose, the collecting tank 30 may have at least one wall of which at least one part 34 is inclined so as to allow a pipette 48, presented vertically, to come and remove the microorganisms collected on the entire surface area of the membrane 32 without striking the wall of the tank 30.

Whatever the embodiment envisioned, and in a nonlimiting manner, the device according to the invention may also be used with a swab for collecting the microorganisms that have been concentrated and retained on the filtering means of the collecting tank, for example a membrane. The collecting by swab can be carried out either manually or automatically with an adaptation of the grasping tool of a pipetting robot.

The device according to the invention also operates with various types of filters used in the prefiltration tank or the collecting tank, alone or stacked, and various membranes alone or stacked.

For certain liquids which are not very complex, the prefiltration tank is not useful. The samples are directly deposited above the filtering means of the collecting tank, for example on a filtration membrane, more particularly on a membrane with a pore size of 0.2 μm. In the case where the prefiltration tank is not useful, said tank can be removed by a pipette-holder or swab-holder tool for a pipetting robot.

Whatever the embodiment envisaged, and in a nonlimiting manner, filtration materials that can be used as filtering means are given by way of examples in table 1. The pore size is adjusted according to the size of the debris to be filtered. The pore size of the material used as filtering means can reach 1 mm so as to make it possible to filter out large debris.

TABLE 1

Example of filtration materials

| Code | Supplier | Material | Pour size (ø in pm) |
|---|---|---|---|
| Grid | | Grid | <1000 (1 mm) |
| Filtrona | Filtrona | | >100 |
| VFE (2 mm) | Whatman | Glass fiber | 5 |
| Pall PAD | Pall | Cellulose | |
| Pall 10 | Pall | PPE | 10 |
| Cotton | Store open to the general public | Cotton | |
| Cotton20 | Prat-Dumas | Cotton | 20 |
| 4 | Whatman | Cellulose | 20-25 |
| 40 | Whatman | Cellulose | 8-12 |
| 41 | Whatman | Cellulose | 12-16 |
| 43 | Whatman | Cellulose | 10-15 |
| 113 | Whatman | Cellulose | 20 |

The filtering means of the prefiltration tank, also called prefilters or prefilter stacks, used in the device according to the invention are also given hereinafter. Alternatively, the materials used as filtering means of the prefiltration tank can be used as filtering means of the collecting tank, alone or stacked.

The device according to the invention, also called double-filtration device, and as previously described, is applied here to the treatment of inoculated urine. In comparative table 2, for each filtering means of the prefiltration tank, 9 ml of a set of mixed urine samples consisting of 10 tubes of pathological urine are introduced onto the filtering means in the prefiltration tank in which a vacuum is gently applied by means of a three-way valve. When the volume has passed through the prefilter(s), the three-way valve is slowly shifted into the Filter position so as to cause the urine to pass through the filtering means of the collecting tank, in this case a 0.45 μm PES membrane. The valve is returned to the closed position.

The bacterial pellet is washed on the membrane with 1 ml of 50 mM carbonate buffer, pH8 (filter valve open), and then recovered with 400 μl of carbonate buffer (vacuum stopped and device returned to atmospheric pressure); the volume recovered ranges from 300 to 400 μl. The volume collected was divided into two parts, including one part for assaying proteins after lysis (lysis protocol P2).

The polymicrobial urines contained predominantly:

*E. aerogenes:* $1.2 \times 10^7$ CFU/ml

*E. coli:* $3 \times 10^6$ CFU/ml

*S. aureus:* $1 \times 10^5$ CFU/ml.

Comparative table 2 recapitulates the observations made during the tests and also the results of counting the number of CFU by counting on bioMérieux chromID® CPS agar plates and the protein assay results.

COMPARATIVE TABLE

| | | prefilters | | | | |
|---|---|---|---|---|---|---|
| Test ref. | Prefilter ref. | Prefiltration time | Filtration time | Washing buffer filtration time | Bacterial pellet recovery volume | Weight of proteins after lysis P2 (μg/test) |
| 1-1 | 2*VFE + filtrona | negligible yellow prefilters | 1 minute Valve problem (cracked) 9 ml filtered | 30 seconds | 340 μl | 63 |
| 1-2 | 2*VFE + Filtrona | negligible yellow prefilters | 3 minutes 9 ml filtered | 50 seconds | 350 μl | 61 |
| 2-1 | PALL10 + COTTON20 + filtrona | negligible clear prefilters | Interruption at 3 min slow + clogging 4.5 ml filtered | 3 min 50 with assistance | 390 μl | 45 |
| 2-2 | PALL10+ COTTON20 + filtrona | negligible clear prefilters | Interruption at 3 min slow + clogging 5 ml filtered | 3 min 50 with assistance | 390 μl | 53 |
| 3-1 | Wattman 43 + 1136 + 4 | rapid but foam In filtration part | 2 min 40 9 ml filtered | 50 seconds | 400 μl | 26 |
| 3-2 | Wattman 43 + 1136 + 4 | PF 4: dirty PF113: dirty PF 43: dirty | Interruption at 3 min slow+ clogging 83 ml filtered | 2 min with assistance | 410 μl | 45 |
| 4-1 | Wattman 43 + 1136 + 4 | rapid? foam present | 2 min 9 ml filtered? | 30 seconds | 300 μl | 21 |
| 4-2 | Wattman 43 + 1136 + 4 | rapid? foam present | membrane torn: pellet not recovered | — | — | |

COMPARATIVE TABLE-continued

| | | | prefilters | | | |
|---|---|---|---|---|---|---|
| 5-1 | PallPAD+ Cottonbb | negligible | 3 min 6 ml filtered | 3 min with assistance | 390 μl | 65 |
| 5-2 | PallPAD + Cottonbb | negligible | 3 min 5.5 ml filtered | 3 min with assistance | 400 μl | 59 |

| Test ref. | Count | Observations on CPS agars | | |
|---|---|---|---|---|
| | | Blue-green | Pink-violet | Beige |
| 1-1 | $>1 \times 10^7$ | number approx equal to pink-violet | number approx equal to blue-green | some |
| 1-2 | $1 \times 10^4$ | number approx equal to pink-violet | number approx equal to blue-green | some |
| 2-1 | $1 \times 10^4$ | number approx equal to pink-violet | number approx equal to blue-green | approx 10 |
| 2-2 | $1 \times 10^5$ | number approx equal to pink-violet | number approx equal to blue-green | approx 10 |
| 3-1 | $1 \times 10^7$ | number approx equal to pink-violet | number approx equal to blue-green | some |
| 3-2 | $1 \times 10^8$ | more than pink-violet | less than blue-green | some |
| 4-1 | $1 \times 10^7$ | predominant | much less than blue-green | some |
| 4-2 | — | — | — | — |
| 5-1 | $1 \times 10^7$ | number approx equal to pink-violet | number approx equal to blue-green | some |
| 5-2 | $1 \times 10^7$ | predominant | less than blue-green | some |

Preferentially, the prefilter stacks that can be used as filtering means of the prefiltration tank are:
2*VFE+Filtrona
Whatmann Paper Filter 43+113+4
Whatmann Paper Filter 40+41+113+4
PallPAD+Cotton.

Whatever the embodiment envisaged, and in a nonlimiting manner, the membranes that can be used, in particular as filtering means of the collecting tank and by way of example, are:
Supor PES 800 membrane (Pall Gelmann)
Supor PES 450 membrane (Pall Gelmann)
Supor PES 200 membrane (Pall Gelmann)
Supor 0.2 Mach V membrane (From Nalgen Filtration Unit)
Express 0.45 (Millipore)
GF/F glass fiber depth filter (Whatman)
Polymer membranes having pore sizes between 0.22 and 1.5 μm, preferentially between 0.22 and 1 μm, more preferentially between 0.22 and 0.8 μm, even more preferentially between 0.22 and 0.45 μm: made of polypropylene, of polyethersulfone (PES), of Nylon (polyamide), of polytetrafluoroethylene (PTFE), of polycarbonate, of polyester, or based on cellulose (regenerated cellulose, cellulose acetate, cellulose nitrate, mixed cellulose ester).
Membranes type Anopore (Anodisc) made of aluminum oxide with pore sizes of 0.02 μm (for applications of exosome purification type).
The filtration membranes may be materials based on silica, polymers, alumina acetate or alumina oxide, by way of example.

The porosity of the filtering means used in the device according to the invention will be easily adjusted by those skilled in the art according to the constituents of interest sought in the biological sample.

Whatever the embodiment envisioned, and in a nonlimiting manner, the swabs that can be used in combination with the use of a pipetting tip are:
swab 1 (VWR) reference 1490241 Flexible swab
swab 2 (Texwipe) reference TX745B Hard swab In this use, the porous part of the swab is dissociated from the shaft so as to wrap the part of a pipetting tip which opens out, which usually pipettes the liquid.

The filtering means of the collecting tank which extends in a second plane can be inclined by an angle other than 30°, i.e. between 10 and 60° (which corresponds to an angle between 30 and 80° relative to the vertical) relative to the plane formed by the base of the fixed support, this being while allowing the samples to be concentrated and to be collected by a collecting means such as a pipette or a swab.

Whatever the embodiment envisioned, and in a nonlimiting manner, the device can be equipped with a $3^{rd}$ tank comprising a third filtering means, this being in order to perform a further filtration stage for sought compounds of which the size is between 0.02 and 0.2 μm, such as microvesicles or exosomes.

The device and corresponding process can be used to collect microorganisms automatically from urine and blood-culture samples and also to extract small biological elements such as exosomes or microvesicles. The device can thus be used in the oncology field by making it possible, for example, to concentrate exosomes (90 nm in diameter), known as a cancer marker. The added value is that of proposing a rapid, generic and simple process for extracting exosomes or microvesicles from saliva, serum or plasma samples. In this process, the filtering means of the collecting tank is a membrane with a pore size of 0.02 μm. Optionally, another embodiment comprises a third tank containing a third filtering means downstream of the filtering means of the collecting tank comprising a membrane with a pore size of 0.02 μm.

EXAMPLES OF USE OF THE DEVICE ACCORDING TO THE INVENTION

The device according to the invention was tested on two types of samples: urine (clinical and inoculated) and blood cultures (clinical and inoculated).

The objective of part of the experiments is to estimate the effectiveness of the device in collecting and restoring microorganisms (microorganism collection yield). A second part of the experiments is carried out until the final analysis by mass spectrometry (ESI or MALDI) in order to identify these microorganisms.

Example 1: Experiments in Inoculated Urine: Results on Three Microorganisms in Automatic Mode Microorganisms EC (*Escherichia coli*), SE (*Staphylococcus epidermidis*) and CA (*Candida albicans*).

TABLE 3

Yield of recovery (%) of the microorganisms E.C, S.E and C.A on several replicates

| Replicate | MO | | |
|---|---|---|---|
| | EC | SE | CA |
| 1 | 100 | 37 | 12 |
| 2 | 78 | 44 | 20 |
| 3 | 88 | 35 | 18 |
| 4 | 92 | 40 | 9 |
| 5 | 91 | 38 | 8 |
| 6 | | | 7 |
| 7 | | | 15 |

The yield is defined as the ratio of the amount of microorganisms recovered on the membrane at the end of the protocol to the amount of microorganisms introduced in solution on the prefilter.

Figure 17:
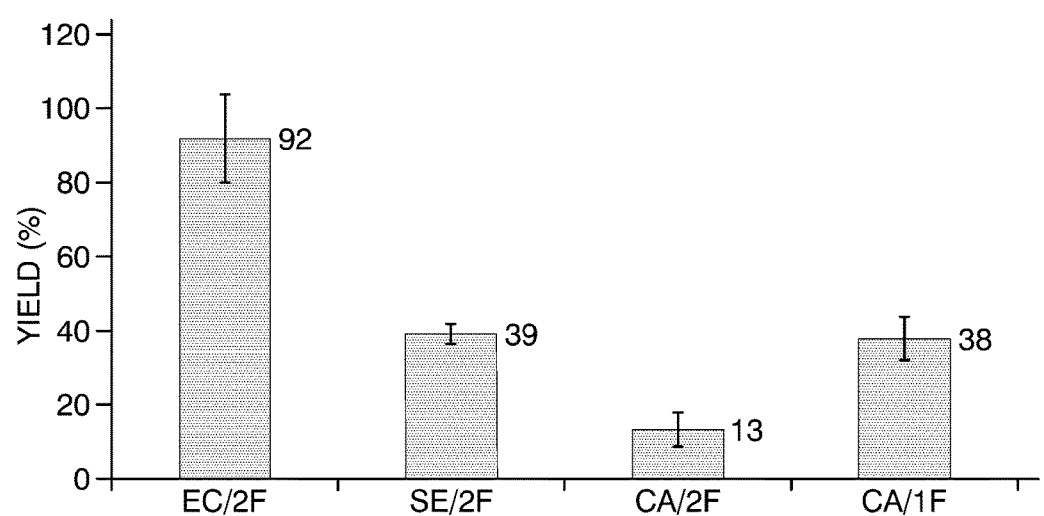
FIG. 17 is a graph illustrating the levels of prefiltration obtained using the device according to the invention for the treatment of various samples of inoculated urine.

This experiment, illustrated in FIG. 17, makes it possible to conclude that the device according to the invention is operating correctly. It makes it possible to effectively filter 10 ml of urine and to collect a not insignificant fraction of the microorganisms therefrom.

Example 2: Experiments in Inoculated Healthy Urine: On Automated Pipetting Device (4 Parallel Devices)

Filtration yield on the EC (*Escherichia coli*) and CA (*Candida albicans*) microorganisms for various resuspension configurations (volume and distance to the vertical of the filter).

| Average yield on 4 samples | EC | CA |
|---|---|---|
| Small-volume jet and distance 1 mm | 69% | 29% |
| Small-volume jet and distance 3 mm | 59% | |
| Large-volume jet and distance 3 mm | 73% | 27% |
| Large-volume jet and distance 5 mm | 59% | |
| Manual reference | 82% | |

Table 4 showing the yield of recovery of the microorganisms E.C and C.A on several replicates while varying the automated resuspension method This experiment made it possible to come to a conclusion regarding the feasibility of automation of the device and regarding the impact of the type of resuspension on the recovery yield.

Example 3: Experiment with Pathological Urine: Results of Detection of *E. coli* Peptides by LC-ESI MS (MRM Mode)

A batch of fifteen pathological urines was treated by double filtration (DF) with the device according to the invention. The filtering means of the prefiltration tank consists of a stack of prefilters (order going from the bottom to the top, the prefilter placed at the top being the first to receive the liquid): Nylon 30 μm/2×VFE 51.1M/Filtrona 2 mm or 4 mm (i.e. 2×2 mm) and the filtering means of the collecting tank is a 0.45 μm PES membrane (Pall). The sequence of the prefiltration/filtration steps for 6 to 10 ml of urine is carried out in at most 3 minutes.

After washing with 1 ml of water, the concentrate was collected by resuspending in 400 μl of carbonate buffer, and then subjected to the lysis-digestion protocol (manual version) so as to be injected into LC-ESI MS with a method of acquisition, developed in a non-optimized manner for searching for peptides that are found in *E. coli*. The MRM method targets 60 peptides, 7 of which are specific for the *E. coli* species and 9 of which are common to the enterobacterial family; the remaining 44 must be generic to Gram- bacteria.

Table 5 shows that, after the double-filtration treatment of urines with very diverse compositions (amount of white blood cells, red blood cells, epithelial cells), the *E. coli* specific peptides are, as a whole, well detected for the urines containing the *E. coli* species according to the provided results of identification on a bioMerieux VITEK®2 automated device. For these same urines, the detection of the peptides common to enterobacteria is also correct since the *E. coli* species belongs to this family. The urines u10 and u13 containing bacteria of the enterobacterial family clearly exhibit peptides specific for this family without the presence of the *E. coli* specific peptides. The urine u9 identified as *C. koseri* results in the detection of *E. coli* specific peptides and the peptides common to the enterobacterial family. This presence of a population of *E. coli* together with *C. koseri* colonies is also observed on bioMerieux ChromID® CPS culture medium.

TABLE 5

| | Observations/identifications given by the hospital | | | | | bioMérieux results LC-ESI-MS/MS MRM EC5 method | | |
|---|---|---|---|---|---|---|---|---|
| | KOVA cells | | | | | N | | |
| urine | Leukocytes (p/μl) | Red blood cells (p/μl) | other parameters | CPS (cfu/ml) | Vitek2 identification(s) | total peptides detected (/60) | E-coli-specific peptides detected (max = 7) | peptides of the enterobacterial familly detected (max = 9) |
| u2 | 400 | <5 | Nothing to report | 10 * 7 | E. coli | 59 | 7 | 9 |
| u5 | 1400 | <5 | Nothing to report | 10 * 7 | E. coli | 59 | 7 | 9 |
| u6 | 950 | 2100 | blood casts | 10 * 7 | E. coli | 59 | 7 | 9 |
| u14 | 3700 | <5 | Nothing to report | 10 * 7 | E. coli | 58 | 7 | 9 |
| u7 | 120 | 230 | Nothing to report | 10 * 7 | E.coli; Enterococcus | 55 | 6 | 9 |
| u9 | 250 | 40 | Nothing to report | 10 * 7 | C. koseri | 48 | 4 | 8 |
| u8 | >5000 | NP | Nothing to report | 10 * 6 | E. coli | 47 | 4 | 7 |
| u15 | >5000 | 400 | Nothing to report | 10 * 7 | E. coli; Enterococcus | 21 | 3 | 5 |
| u1 | >5000 | NP | Nothing to report | 10 * 7 | E. coli | 27 | 1 | 5 |
| u10 | 2600 | 130 | Yeasts | 10 * 7 | E. cloacae, C. albicans, C. non albicans | 35 | 0 | 8 |
| u13 | 3700 | <5 | Nothing to report | 10 * 7 | Morganella morganii | 25 | 0 | 5 |
| u4 | 850 | <5 | Nothing to report | 10 * 6 | E. coli | 2 | 0 | 0 |
| u3 | 240 | 1400 | Epithelial cells | 10 * 4 | polymicrobial | 7 | 0 | 0 |
| u11 | >5000 | 670 | Nothing to report | 10 * 3 | polymicrobial | 1 | 0 | 0 |
| u12 | 390 | 90 | Nothing to report | 0 | sterile | 3 | 0 | 0 |

Table 6 gives the scores for correct identification of the *E. coli* species in a first batch of pathological urines.

TABLE 6

| Batch | ESI-MS/MS results 7 E.coli-specific peptides | | | | | |
|---|---|---|---|---|---|---|
| No. one. Urines con-taining E. coli | peptides detected with score ≥ 3 (/7) | | peptides detected 1 ≤ score < 3 (/7) | | peptides not detected | |
| | N urines | (%) | N urines | (%) | N urines | (%) |
| total | 10 | 8 | 80% | 1 | 10% | 1 | 10% |
| Mono | 5 | 4 | 80% | 1 | 20% | | 0% |
| Bimicrobial | 5 | 4 | 80% | | 0% | 1 | 20% |

A second batch of pathological urines gave results confirming the effectiveness of our protocol for preparing samples upstream of LC-ESI MS analyses in targeted mode as illustrated by table 7 for the five urines that contained the *E. coli* species.

TABLE 7

| | ESI-MS/MS results 7 E. coli-specific peptides | | | | |
|---|---|---|---|---|---|
| Batch No. two. Urines containing E. coli | peptides detected with score ≥3 (/7) | | peptides detected 1≤ score <3 (/7) | | |
| | N urines | (%) | N urines | (%) | |
| total | 5 | 4 | 80% | 1 | 20% |
| Mono | 2 | 1 | 50% | 1 | 50% |
| Bimicrobial | 3 | 3 | 100% | | 0% |

Experiment with Pathological Urines: Results of Identification by MALDI-TOF

Fifteen pathological urines were treated by double filtration with the device according to the invention with, as filtering means of the prefiltration tank, a stack of prefilters (order going from bottom to top, the prefilter placed at the top being the first to receive the liquid): 2×VFE 5 μm/Filtrona 2 mm and, as filtering means of the collecting tank, a 0.45 μm PES membrane (Pall). After the retention of the microorganisms on the membrane, said microorganisms were washed once with 1 ml of water and then collected by carrying out about thirty suction/discharge operations or dispensing/resuctioning operations with 400 μl of water. The suspensions obtained were centrifuged for 5 min at 10 000 g in order to sediment the microorganisms and to remove the supernatant. The bacterial pellet was deposited on a MALDI-TOF target before addition of the α-cyano-4-hydroxycinnamic acid matrix (HCCA matrix) or with the addition of formic acid (FA), drying and then addition of the HCCA matrix. The MALDI-TOF spectra were obtained with a Shimadzu spectrometer controlled by Launchpad (bioMerieux VITEK® MS apparatus). The results of identifications given according to table 8 were obtained by interrogating the "bacteria" database.

TABLE 8

| No | Leukocytes (p/μl) | Red blood cells (p/μl) | VITEK2 CFU/ml | identification | BioMérieux observations CFU/ml at reception | Contamination level | Manual dual filtration + MALDI-ToF identification Interrogation VITEK MS base CLI_2.0.0 P1: DF + HCCA | P2: DF + FA + HCCA |
|---|---|---|---|---|---|---|---|---|
| 80 | >5000 | <5 | 1E+07 | ENT.CLC | 1.E+07 | B* | ENT.CLC and ENT.ASB | ENT.CLC and ENT.ASB |
| p66 | 570 | <5 | 1E+07 | ESC.COL | 1.E+07 | B majo | ESC.COL | ESC.COL |
| p67 | >5000 | <5 | 1E+07 | ESC.COL | 1.E+07 | B majo | ESC.COL | ESC.COL |
| p69 | >5000 | 900 | 1E+07 | ESC.COL | 1.E+07 | M | ESC.COL | ESC.COL |
| p71 | >5000 | <5 | 1E+06 | ESC.COL | 1.E+06 | B majo | ESC.COL | ESC.COL |
| p75 | 2000 | <5 | 1E+07 | ESC.COL | 1.E+07 | M | ESC.COL | ESC.COL |
| 76 | 1600 | <5 | 1E+07 | PRT.MIR | 1.E+07 | B majo | PRT.MIR | PRT.MIR |
| p70 | >5000 | <5 | 1E+07 | ESC.COL + ENC.FEC | 1.E+07 | B* | ENC.FEC | ESC.COL |
| p64 | ND | >5000 | 1E+07 | PSD.AEU + ENC.FEC | 1.E+07 | B* | PSD.AEU | PSD.AEU |
| p65 | 700 | >5 | 1E+07 | polymorphic flora | 1.E+07 | P | KLB.OXY | No ID |
| 79 | 740 | 23 | 1E+03 | polymorphic flora | 1.E+04 | P | No ID | Low discrim |
| p68 | 210 | <5 | 0E+00 | sterile | 1e3/1e4 | S | coryn. Urealyticum or Low discrim | Low discrim |
| p73 | 50 | 1100 | 1E+03 | sterile | 1e3/1e4 | S | No ID | No ID |
| 77 | 90 | <5 | 0E+00 | sterile | 0.E+00 | S | No ID | No ID |
| 78 | 330 | <5 | 1E+03 | sterile | 0.E+00 | S | No ID | No ID |

B* = bimicrobial urines with 2 species at similar concentrations.

The identification results can be presented as follows (see also table 9):
13 standard urines are exploited:
4 sterile,
2 monomicrobial,
4 bimicrobial (with a major species),
and 3 bimicrobial (with two species of similar concentrations).

Depending on the method of deposition on the MALDI target (HCCA without FA (formic acid) and with FA before the addition of HCCA), 90% and 100% correct identification were obtained at the species level (on this panel of 10 urines, the positives of which are at least at $10^6$ CFU/ml).

For the 3 bimicrobials (with two species of close concentrations), only one species can be identified at a time on a deposit.

These results clearly illustrate that a rapid double filtration of the crude urines using the device according to the invention makes it possible to sufficiently purify and collect enough microorganisms for an exact identification of said organisms by MALDI-TOF.

Example 4: Experiment with Inoculated Blood Cultures: Results of Peptide Detection by LC-ESI MS (MRM Mode)

The lysis-filtration protocol consists briefly of a selective lysis of the blood cells by action of a buffer containing a surfactant for a short period of time.

The advantage provided by the device described herein is by virtue of its geometry, in this case an incline of the filtering means of the collecting tank of 30°, which allows effective harvesting of the microorganisms by means of a liquid solution which finally results in a bacterial suspension.

The lysis-filtration protocol is the following:
The filtration is carried out on a 0.2 μm PES filtration membrane used as filtering means of the collecting tank on the device according to the invention.
The test sample is 0.8 ml of blood culture which is treated with 0.4 ml of 0.3 M CAPS buffer/0.45% Brij for 2 minutes, followed by filtration for 2 minutes.
3 washes with 175 μl of wash buffer 1 (0.45% NaCl/ 0.005% Brij 97).
1 wash with 175 μl of wash buffer 2 (wash buffer 2: 0.005% Brij 97)

TABLE 9

Correct identifications by MALDI-ToF versus Vitek2

| Protocole | N urines | Sterile (S) | Monomicrobial (M) | Bimicrobial with 1 predominant species (B) | Score (S + M + B) | Bimicrobials 2 species of Identical concentration Identif. of 1 species | Identif. of the 2 species |
|---|---|---|---|---|---|---|---|
| P1: DF + HCCA | 13 | 3/4 | 2/2 | 4/4 | 9/10 (90%) | 3/3 | 0/3 |
| P2: DF + FA + HCCA | 13 | 4/4 | 2/2 | 4/4 | 10/10 (100%) | 3/3 | 0/3 |

Figure 18:
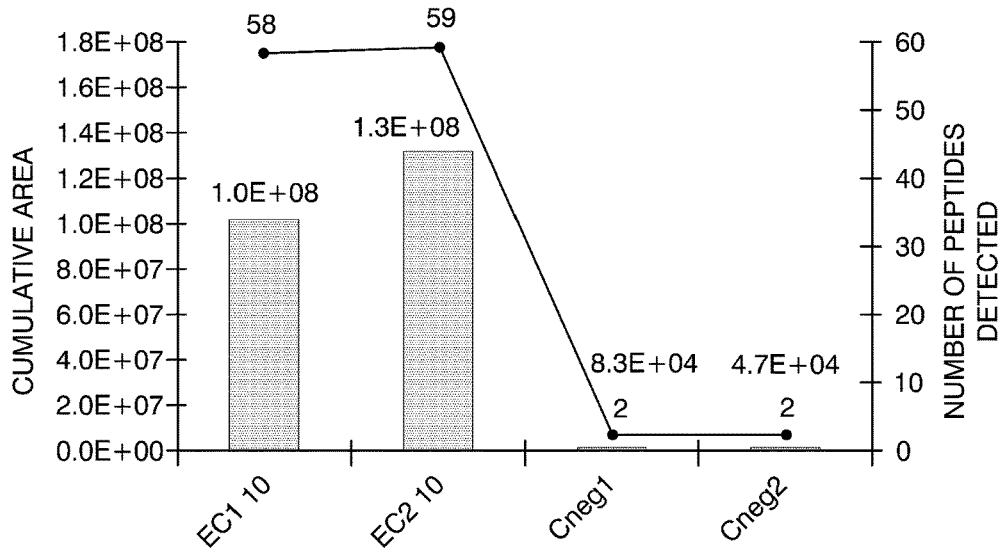
FIG. 18 comprises three graphs showing the ESI-MS detection of peptides specific for the species inoculated in blood culture bottles in comparison with a negative control (sterile blood culture). This
Figure 18:
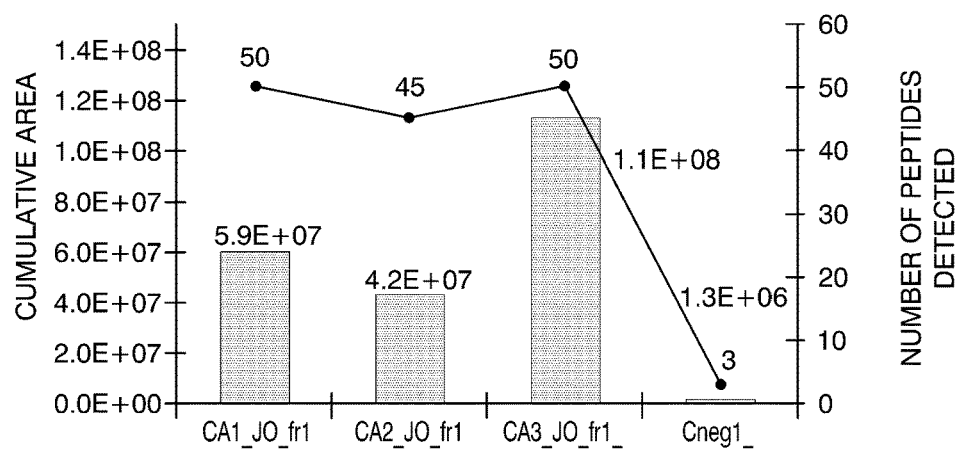
Figure 18:
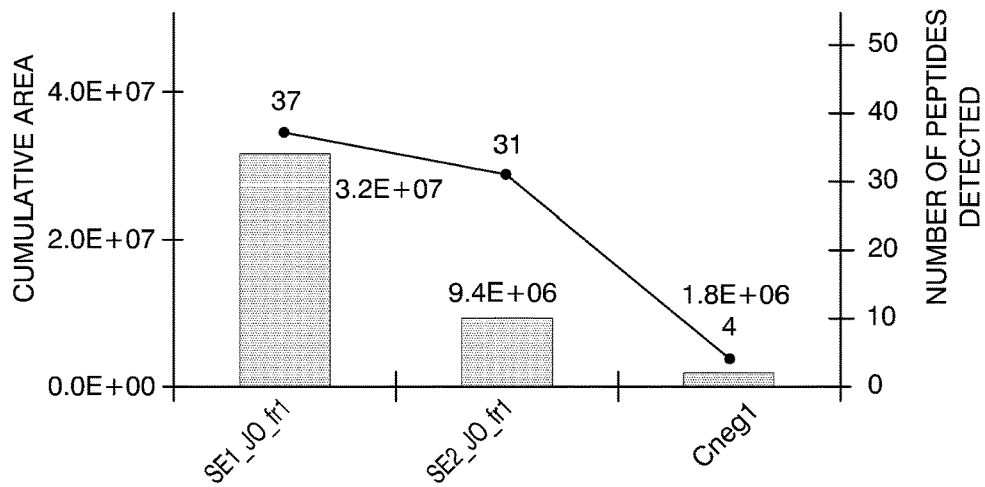

The collecting is carried out with 200 µl of carbonate buffer, adhering to a constant number of suctions/discharge operations (30) or dispensing/resuctioning operations (30). Repetition of the collecting, a $2^{nd}$, a $3^{rd}$ and a $4^{th}$ time on the same membrane was also tested. The lysis-digestion was carried out with P2A on a Hamilton pipetting robot. The demonstration was carried out for *E. coli, S. epidermidis* and *C. albicans* with correct detection of the peptides targeted by the MRM method. FIG. 18 presents the results of detection via the MRM methods adapted to the microorganism inoculated in the blood culture bottles. The three graphs show, for the 3 microorganisms, the correct detection of the specific peptides in the positive samples at $D_0$ post-culture (EC1 $D_0$, EC2 $D_0$, CA1 $D_0$, CA2 $D_0$, CA3 $D_0$, SE1 $D_0$, SE2 $D_0$, SE3 $D_0$). A minor number of peptides (2 to 4) are detected in the negative controls (Cneg). The significant difference both in the number of peptides detected and in the cumulative area between the positive samples and the negative controls indicates that the protocol carried out on the device described clearly makes it possible to harvest the bacteria contained in the blood cultures.

Other blood cultures were also treated in the same way, but, after collection of the microorganisms, the protocol $I_0$ was carried out in order to identify by LC-ESI-MS using the protein profiles. The results presented in table 10 show that the 8 *E. coli* blood cultures were clearly identified by LC-ESI with the Cross-Cor algorithm with the urine database being interrogated, but that there is confusion with *Shigella* if it is the culture base that is interrogated, since the species are close. The four blood cultures with yeasts (*C. albicans*) are correctly identified (out of four). A single *S. epidermidis* blood culture is clearly identified (out of four). Despite these few cases of incorrect identifications, these tests attest to the effectiveness of the preparation of sample by lysis-filtration carried out on the device according to the invention.

Alternative Process on Urine Sample Using the Device According to the Invention:

The various steps of the manipulation are given below:
1) Upon reception, the urines are photographed.
2) The volumes in the tubes are estimated (compared to a graduated tube).
3) 10 µl are deposited on bioMerieux ChromID® CPS agar for verification.
4) 150 µl were set aside at 4° C. for plating out of 100 µl on COS for 5 h of growth.
5) The rest of the sample was treated with the device according to the invention. The filtering means of the prefiltration tank consists of a stack of prefilters, the prefilters used being, from bottom to top: 1×VFE 5 µm/Filtrona 2 mm. The filtering means of the collecting tank where the bacteria will be recovered is a membrane: 0.45 µm PES (Pall).
6) The volume of urine filtered is between 3 and 6 ml for a filtration time of a few minutes. The concentrate is collected with 1000 µl of water (Versol).
7) At the end of the manual protocol, 10 µl are plated out on bioMerieux ChromID® CPS agar so as to be able to see whether the bacterial population is the same between the collected fraction and the starting urine (colony color, polymorphism, count comparison before/after double filtration).
8) For the remaining volume of the fractions collected, a centrifugation for 5 min at 10 000 g was carried out in order to remove the maximum amount of supernatant (water) and to keep a pellet of a few µl for MALDI-TOF.
9) The deposits on a MALDI-TOF plate were carried out in duplicate according to the terminology of table 11.
10) The manipulation by short culture of 5 h is carried out by depositing 100 µl of urine and plating out with a scraper. After 5 h of growth at 37° C., the biofilm is observed. This biofilm is then collected with a 1 µl loop and deposited on a MALDI-TOF target.

TABLE 10

Results of identification by LC-ESI MS after lysis-filtration on the device as described and extraction of protein $I_0$ (mode full scan, protein profile)

| | Non diluted | | | | Diluted 10x | | | |
|---|---|---|---|---|---|---|---|---|
| | pic_crossCor BaseUrine | sum_nnls BaseUrine | pic_crossCor BaseCulture | sum_nnls BaseCulture | pic_crossCor BaseUrine | sum_nnls BaseUrine | pic_crossCor BaseCulture | sum_nnls BaseCulture |
| CAN.ALB_001 | TRUE | TRUE | TRUE | TRUE | TRUE | CAN.TROP | TRUE | BAC.CEU |
| CAN.ALB_002 | TRUE | CAN.TROP | TRUE | TRUE | TRUE | CAN.TROP | TRUE | BAC.CEU |
| CAN.ALB_003 | TRUE | CAN.TROP | TRUE | TRUE | TRUE | CAN.TROP | TRUE | BAC.CEU |
| CAN.ALB_004 | TRUE | CAN.TROP | TRUE | TRUE | TRUE | CAN.TROP | TRUE | BAC.CEU |
| ESH.COL_001 | TRUE | TRUE | SHG.BOY | ENT.CLC | TRUE | CAN.GLB | SHG.BOY | BAC.CEU |
| ESH.COL_002 | TRUE | ENT.AER | SHG.FLX | ENT.CLC | TRUE | CAN.GLB | SHG.FLX | BAC.CEU |
| ESH.COL_003 | TRUE | ENT.AER | SHG.FLX | ENT.CLC | TRUE | CAN.GLB | SHG.SON | CAN.ALB |
| ESH.COL_004 | TRUE | ENT.AER | SHG.FLX | ENT.CLC | TRUE | CAN.GLB | SHG.BOY | BAC.CEU |
| ESH.COL_005 | TRUE | ENT.AER | SHG.BOY | ENT.CLC | TRUE | CAN.GLB | SHG.FLX | CAN.ALB |
| ESH.COL_006 | TRUE | ENT.AER | SHG.SON | ENT.CLC | TRUE | CAN.GLB | SHG.SON | BAC.CEU |
| ESH.COL_007 | TRUE | ENT.AER | SHG.FLX | ENT.CLC | TRUE | CAN.GLB | SHG.FLX | CAN.ALB |
| ESH.COL_008 | TRUE | ENT.AER | SHG.SON | ENT.CLC | TRUE | CAN.GLB | SHG.BOY | CAN.ALB |
| STA.EPI_001 | STA.AUA | TRUE | STA.AUA | TRUE | CAN.TRO | CAN.TRO | STR.ORA | BAC.CEU |
| STA.EPI_002 | STA.AUA | CAN.TROP | BAC.CEU | CAN.ALB | CAN.GLB | CAN.GLB | BAC.CEU | BAC.CEU |
| STA.EPI_003 | PRT.MIR | TRUE | YER.ETC | TRUE | STA.AUA | CAN.TRO | BAC.CEU | BAC.CEU |
| STA.EPI_004 | TRUE | CAN.TROP | TRUE | CAN.ALB | STA.AUA | CAN.GLB | STA.AUA | BAC.CEU |
| HEM.NEG0013453 | ENT.AER | CAN.TROP | STR.ORA | BAC.CEU | CIT.KOS | NA | STR.ORA | NA |
| HEM.NEG0013454 | ENT.AER | CAN.TROP | STR.ORA | BAC.CEU | ENT.AER | NA | CIT.BRA | NA |
| 16 | 13 | 4 | 5 | 6 | 12 | 0 | 4 | 0 |
| Correct Identifications (%) | 81.25 | 25 | 31.25 | 37.5 | 75 | 0 | 25 | 0 |

TABLE 11

Codification of the protocols according to the treatment carried out and the method of deposition on MALDI-TOF target

| Protocol 1 (P1): double filtration + HCCA | Protocol 2 (P2): double filtration + FA + HCCA |
| Protocol 5 (P5): culture on COS 5H + HCCA | Protocol 6 (P6): culture on COS 5H + FA + HCCA |

HCCA : (α-cyano-4-hydroxycinnamic acid): 1 µl per spot
FA: (formic acid): 0.5 µl per spot
double filtration: treatment using the device according to the invention

The invention claimed is:

1. A device for preparing a biological sample, comprising:
a fixed support comprising a base that extends in a first plane, and an upper surface opposed to and inclined relative to the first plane of the base,
a filtration block on the upper surface and configured to be removable from the fixed support,
the filtration block comprising a collecting tank, the collecting tank comprising a wall and a filtering device, the filtering device extending in a second plane and dividing the collecting tank into a collection area that retains the biological sample before passing through the filtering device, and a suction area, the suction area being configured to be connected to a suction device,
wherein the second plane of the filtering device is inclined relative to the first plane of the base of the fixed support, and
the fixed support is fixed relative to the incline of the second plane.

2. The device as claimed in claim 1, wherein the filtration block further comprises a prefiltration tank that is configured to be removable from the filtration block,
the prefiltration tank comprising a filtering device dividing the prefiltration tank into a collection area that retains the biological sample before passing through the filtering device and a suction area,
the suction area of the prefiltration tank being in fluidic communication with the collection area of the collecting tank.

3. The device as claimed in claim 2, the suction area of the prefiltration tank configured to be connected to a second suction device.

4. The device as claimed in claim 1, wherein the wall of the collecting tank in the collection area is partly inclined relative to the first plane of the base of the fixed support.

5. The device as claimed in claim 1, the filtering device of the collecting tank comprising at least one membrane with a pore size of between 0.02 and 1.5 µm.

6. The device as claimed in claim 2, the filtering device of the prefiltration tank comprising at least one filter with a pore size of between 5 µm and 1000 µm.

7. The device as claimed in claim 6, the filtering device of the prefiltration tank comprising a stack of filters.

8. The device as claimed in claim 1, the second plane of the filtering device of the collecting tank being inclined relative to the first plane of the base of the fixed support by an angle of between 10° and 60°.

9. The device as claimed in claim 1, the collecting tank comprising an upper part and a lower part that cooperate to hold the filtering device of the collecting tank.

10. The device as claimed in claim 2, the prefiltration tank comprising an upper part and a lower part that cooperate to hold the filtering device of the prefiltration tank.

11. The device as claimed in claim 2, the prefiltration tank comprising a device capable of cooperating with a tool for a pipetting robot.

12. The device as claimed in claim 1, the suction device is a suction/discharge means.

13. The device as claimed in claim 1, the wall of the collecting tank and the filtering device forms a preferential collection area within the filtration block.

14. A process for treating a biological sample including microorganisms using a device as claimed in claim 1, comprising:
depositing the biological sample on the filtering device of the collecting tank,
suctioning the biological sample through the filtering device of the collecting tank, using the suction device connected to the suction area of the collecting tank, and
collecting microorganisms in the biological sample on the filtering device of the collecting tank.

15. A process for treating a biological sample including microorganisms using a device as claimed in claim 2, comprising:
depositing the biological sample on the filtering device of the prefiltration tank,
suctioning the biological sample through the filtering device of the prefiltration tank so as to deposit the biological sample on the filtering device of the collecting tank using the suction device connected to the suction area of the collecting tank,
suctioning the biological sample through the filtering device of the collecting tank using the suction device connected to the suction area of the collecting tank, and
collecting microorganisms in the biological sample on the filtering device of the collecting tank.

16. A process for treating a biological sample including microorganisms using a device as claimed in claim 3, comprising:
depositing the biological sample on the filtering device of the prefiltration tank,
suctioning the biological sample through the filtering device of the prefiltration tank so as to deposit the biological sample on the filtering device of the collecting tank using the second suction device connected to the suction area of the prefiltration tank,
suctioning the biological sample through the filtering device of the collecting tank using the suction device connected to the suction area of the collecting tank, and
collecting the microorganisms in the biological sample on the filtering device of the collecting tank.

17. A device for preparing a biological sample, comprising:
a fixed support comprising a base that extends in a first plane, and an upper surface,
a filtration block on the upper surface of the fixed support and configured to be removable from the fixed support,
the filtration block comprising a collecting tank, the collecting tank comprising a wall extending perpendicularly relatively to the upper surface, and a filtering device, the filtering device extending in a second plane and dividing the collecting tank into a collection area that retains the biological sample before passing through the filtering device, and a suction area, the suction area being configured to be connected to a suction device, wherein the filtering device is inclined relative to the upper surface and inclined relative to the wall of the collecting tank at an angle, and the angle at which the filtering device is inclined relative to the upper surface and inclined relative to the wall of the collecting tank is fixed.

* * * * *